US012605382B2

(12) United States Patent
Jang

(10) Patent No.: US 12,605,382 B2
(45) Date of Patent: Apr. 21, 2026

(54) PHARMACEUTICAL COMPOSITION FOR PREVENTING, ALLEVIATING, OR TREATING CANCER CONTAINING 2,6-DICHLORO-4-(4-(4-HYDROXYCY CLOHEXYLAMINO)-7H-PYRROLO[2,3-D]PYRIMIDIN-5-YL)PHENOL AS ACTIVE INGREDIENT

(71) Applicant: JBKLAB CO., LTD., Seongnam-si (KR)

(72) Inventor: Bong Keun Jang, Seongnam-si (KR)

(73) Assignee: JBKLAB Co., Ltd., Seongnam-si (KR)

( * ) Notice: Subject to any disclaimer, the term of this patent is extended or adjusted under 35 U.S.C. 154(b) by 386 days.

(21) Appl. No.: 18/288,896

(22) PCT Filed: May 3, 2022

(86) PCT No.: PCT/KR2022/006339

§ 371 (c)(1),
(2) Date: Oct. 30, 2023

(87) PCT Pub. No.: WO2022/235054

PCT Pub. Date: Nov. 10, 2022

(65) Prior Publication Data

US 2024/0207271 A1 Jun. 27, 2024

(30) Foreign Application Priority Data

May 3, 2021 (KR) ........................ 10-2021-0056988

(51) Int. Cl.

| | |
|---|---|
| ***A61K 31/519*** | (2006.01) |
| ***A61K 31/365*** | (2006.01) |
| ***A61K 31/44*** | (2006.01) |
| ***A61K 33/243*** | (2019.01) |
| ***A61P 35/00*** | (2006.01) |

(52) U.S. Cl.

CPC .......... *A61K 31/519* (2013.01); *A61K 31/365* (2013.01); *A61K 31/44* (2013.01); *A61K 33/243* (2019.01); *A61P 35/00* (2018.01)

(58) Field of Classification Search

CPC .. A61K 31/519; A61K 33/243; A61K 31/365; A61P 35/00

See application file for complete search history.

(56) References Cited

U.S. PATENT DOCUMENTS

| | | | |
|---|---|---|---|
| 2008/0194557 A1 | 8/2008 | Barbosa et al. | |
| 2016/0233382 A1 | 8/2016 | Yom | |
| 2021/0309665 A1 | 10/2021 | Jang et al. | |

FOREIGN PATENT DOCUMENTS

| | | | |
|---|---|---|---|
| EP | 3533796 | 9/2019 | |
| KR | 10-2015-0108339 A | 9/2015 | |
| KR | 10-2020-0012168 A | 2/2020 | |
| WO | WO 98/07726 | 2/1998 | |
| WO | WO2007/061882 | 5/2007 | |
| WO | WO2020/022636 | 1/2020 | |
| WO | WO-2020022636 A1 * | 1/2020 | ........... C07D 487/04 |

OTHER PUBLICATIONS

WO 2020022636 A1 Machine translation (Year: 2020).*

Shargh, V.H., et al. "Albumin hybrid nanoparticles loaded with tyrosine kinase A inhibitor GNF-5837 for targeted inhibition of breast cancer cell growth and invasion," *International Journal of Pharmaceutics*, 515(1-2):527-534 (Dec. 30, 2016).

Heinen et al., "Trk inhibition reduces cell proliferation and potentiates the effects of chemotherapeutic agents in Ewing sarcoma," *Oncotarget* 7.23: 34860-34880, 2016.

International Preliminary Report on Patentability issued by the Korean Intellectual Property Office as International Searching Authority in PCT Application No. PCT/KR2022/006339, completed on Sep. 19, 2023 (5 pages).

International Search Report and Written Opinion issued by the Korean Intellectual Property Office as International Searching Authority in PCT Application No. PCT/KR2022/006339, mailed on Aug. 10, 2022 (10 pages), with English translation of International Search Report (4 pages).

Zaharia and Gomez, "Triple negative breast cancer: a difficult disease to diagnose and treat," *Rev Peru Med Exp Salud Publica*. 30.4: 649-656, Oct.-Dec. 2013 (w/English translation of abstract).

Hong, D.S. et al., "Larotrectinib in adult patients with solid tumours: a multi-centre, open-label, phase I dose-escalation study," *Annals of Oncology*, 30(2):325-331 (Feb. 2019) (published online Jan. 8, 2019).

Landman, Yosef et al., "Rapid Response to Larotrectinib (LOXO-101) in an Adult Chemotherapy-Naive Patients with Advanced Triple-Negative Secretory Breast Cancer Expressing ETV6-NTRK3 Fusion," *Clinical Breast Cancer*, 18(3):e267-e270 (Jun. 2018) (published online Nov. 28, 2017).

(Continued)

*Primary Examiner* — Sarah Pihonak
*Assistant Examiner* — Mikhail O'Donnel Robinson
(74) *Attorney, Agent, or Firm* — Klarquist Sparkman, LLP

(57) ABSTRACT

The present invention relates to a pharmaceutical composition for preventing or treating cancer, containing 2,6-dichloro-4-(4-(4-hydroxycyclohexylamino)-7H-pyrrolo[2,3-D]pyrimidin-5-yl)phenol as an active ingredient. It has been ascertained that the present invention inhibits the formation of mammospheres in a breast cancer cell line and, when compared to anticancer drugs sorafenib and etoposide, which are topoisomerase inhibitors widely used in lung cancer, ovarian cancer, colon cancer, melanoma and the like, exhibits remarkable effects greater than or equal to those of the anticancer drugs sorafenib and etoposide. In addition, a compound of example 1, according to the present invention, exhibits synergistic anticancer effects when combined with radiotherapy or other anticancer drugs in a breast cancer cell line and a liver cancer cell line, and thus can be developed as an anticancer drug or a food exhibiting excellent effects in the treatment of cancer.

12 Claims, 20 Drawing Sheets

(56) References Cited

OTHER PUBLICATIONS

Miao, Qu et al. "Targeting tropomyosin receptor kinase for cancer therapy," *European Journal of Medicinal Chemistry*, 175:129-148 (Aug. 2019) (published online Apr. 30, 2019).

* cited by examiner

A549; human non-small cell lung cancer cells
SK-OV-3; human ovarian cancer cells
SK-MEL-2; human melanoma cells
HCT15; human colorectal cancer adnocarcinoma cells
Etoposide; cytotoxic anticancer drug, topoisomerase inhibitor

PHARMACEUTICAL COMPOSITION FOR PREVENTING, ALLEVIATING, OR TREATING CANCER CONTAINING 2,6-DICHLORO-4-(4-(4-HYDROXY CYCLOHEXYLAMINO)-7H-PYRROLO[2,3-D]PYRIMIDIN-5-YL)PHENOL AS ACTIVE INGREDIENT

CROSS REFERENCE TO RELATED APPLICATIONS

This is the U.S. National Stage of International Application No. PCT/KR2022/006339, filed May 3, 2022, which in turn claims the benefit of Korean Patent Application No. 10-2021-0056988, filed May 3, 2021. The Korean patent application is incorporated herein in its entirety.

BACKGROUND OF THE INVENTION

1. Field of the Invention

The present invention relates to a pharmaceutical composition for preventing or treating cancer, containing 2,6-dichloro-4-(4-(4-hydroxycyclohexylamino)-7H-pyrrolo[2,3-D]pyrimidin-5-yl)phenol as an active ingredient.

2. Description of the Related Art

Despite the fact that the incidence of cancer has been increasing with the development of civilization, the treatment of cancer patients still relies on surgical operations, radiation therapy, and chemotherapy by administering anticancer drugs with strong cytotoxicity. However, these treatments are generally limited to patients with early-stage cancer or specific types of cancer and cause various side effects, so there is a need to develop anticancer drugs that are effective and have fewer side effects while having a safety profile.

In particular, the breast cancer market is known to be a field with unmet medical needs that lack high anticancer effectiveness and safety. Regarding breast cancer treatment, therapies with various mechanisms targeting patients with different disease characteristics, such as hormone therapy, chemotherapy, and targeted therapy, are being introduced, but there is a steady clinical demand for therapies with excellent anti-cancer efficacy and safety. Among these, triple-negative breast cancer (TNBC), which accounts for 16% of all breast cancers, is difficult to treat due to the poor prognosis after treatment, and there are not enough therapies available to target TNBC (Non-patent reference 1, Rev Peru Med Exp Salud Publica. October-December 2013; 30(4): 649-56).

Currently, treatments for breast cancer including therapies that inhibit the human epidermal growth factor receptor 2 (hereinafter referred to as ‘HER2’) gene, which is involved in tumor growth, and anti-hormonal drugs are widely used. However, in the case of TNBC, HER2 receptor, estrogen receptor, and progesterone receptor are all negative, so it does not respond to existing anticancer drugs. Accordingly, a new targeted treatment that can treat safely and efficiently is urgently needed.

Thus, the present inventors have studied using various cancer cell lines and completed the pharmaceutical composition of the present invention, which can be used as a safe and effective anticancer drug.

SUMMARY OF THE INVENTION

It is an object of the present invention to provide a pharmaceutical composition for preventing or treating cancer.

It is another object of the present invention to provide a health functional food composition for preventing or treating cancer.

It is another object of the present invention to provide a pharmaceutical kit for preventing or treating cancer.

It is another object of the present invention to provide a combination of radiation and anticancer agents for preventing or treating cancer.

It is another object of the present invention to provide a method for treating cancer, comprising a step of administering to a subject in need thereof.

It is another object of the present invention to provide a compound for preventing or treating cancer.

It is another object of the present invention to provide a use of a compound for the preparation of a medicament for use in the prevention or treatment of cancer.

To achieve the above objects, in an aspect of the present invention, the present invention provides a pharmaceutical composition for preventing or treating cancer comprising a compound represented by formula 1 described herein, a stereoisomer thereof, a solvate thereof, a hydrate thereof, or a pharmaceutically acceptable salt thereof as an active ingredient.

In another aspect of the present invention, the present invention provides a health functional food composition for preventing or ameliorating cancer comprising a compound represented by formula 1 described herein as an active ingredient.

In another aspect of the present invention, the present invention provides a pharmaceutical kit for preventing or treating cancer comprising a first component containing a pharmaceutically effective amount of an anticancer agent; and a second component containing a compound represented by formula 1 described herein, a stereoisomer thereof, a solvate thereof, a hydrate thereof, or a pharmaceutically acceptable salt thereof as an active ingredient.

In another aspect of the present invention, the present invention provides a combination of radiation and anticancer agents for preventing or treating cancer.

In another aspect of the present invention, the present invention provides a method for treating cancer, comprising a step of administering a compound represented by formula 1 described herein to a subject in need thereof.

In another aspect of the present invention, the present invention provides a compound represented by formula 1 described herein for use in the prevention or treatment of cancer.

In another aspect of the present invention, the present invention provides a use of a compound represented by formula 1 described herein for the preparation of a medicament for use in the prevention or treatment of cancer.

Advantageous Effect

It has been ascertained that the compound of Example 1 of present invention inhibits the formation of mammospheres in a breast cancer cell line and, when compared to anticancer drugs sorafenib and etoposide, which are topoisomerase inhibitors widely used in lung cancer, ovarian cancer, colon cancer, melanoma and the like, exhibits remarkable effects greater than or equal to those of the anticancer drugs sorafenib and etoposide. In addition, the compound of Example 1, according to the present invention, exhibits synergistic anticancer effects when combined with radiotherapy or other anticancer drugs in a breast cancer cell line and a liver cancer cell line, and thus can be developed as an anticancer drug or a food exhibiting excellent effects in the treatment of cancer.

DESCRIPTION OF THE PREFERRED EMBODIMENTS

Figure 1:
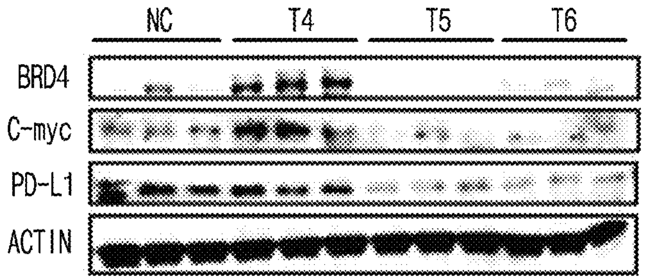
FIG. 1 is a diagram showing the evaluation of the ability to inhibit expression of major proteins.
Figure 2A:
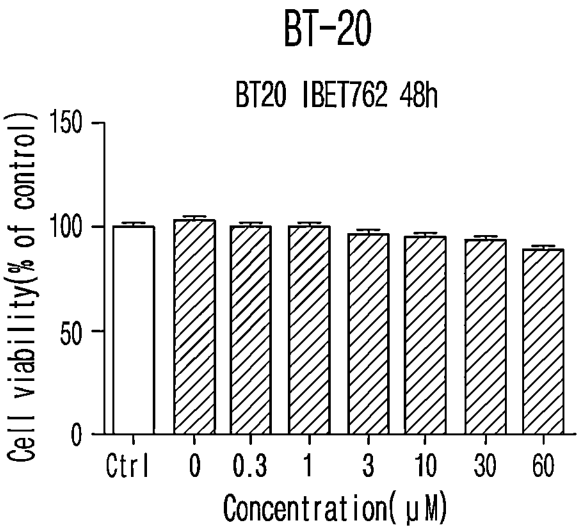
FIGS. 2A-2B are graphs showing the cell viability of BT20, a human-derived breast cancer cell line, after 48 hours of treatment with the compound of Example 1 in culture.
Figure 2B:
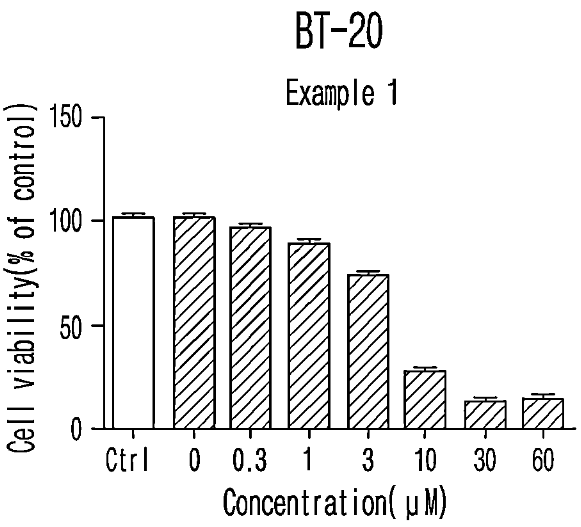
Figure 3A:
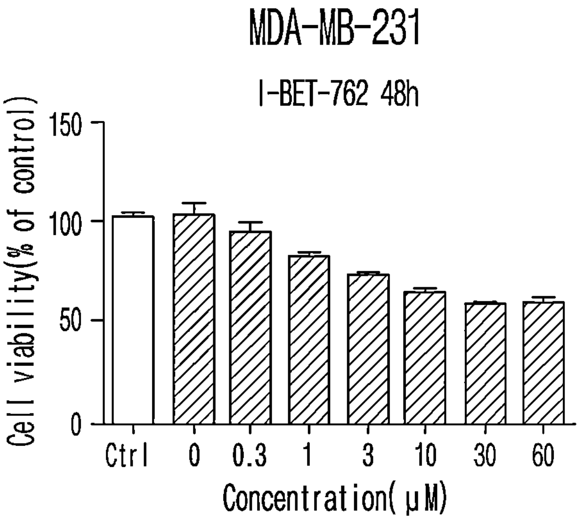
FIGS. 3A-3B are graphs showing the cell viability of MDA-MB-231, a TNBC cell line, after 48 hours of treatment with the compound of Example 1 in culture.
Figure 3B:
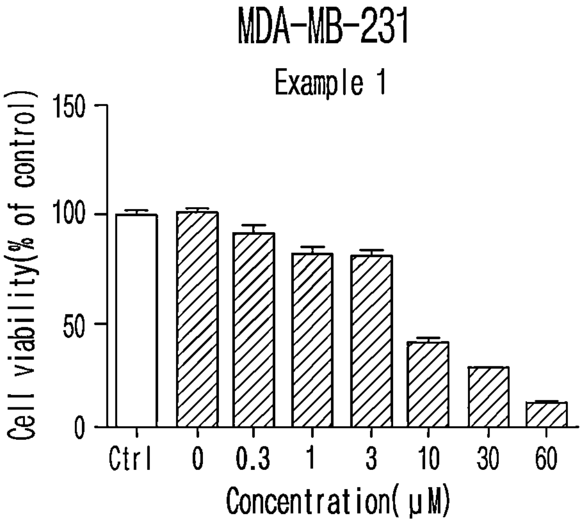

Hereinafter, the present invention is described in detail. The embodiments of this invention can be modified in various other forms, and the scope of the present invention is not limited to the embodiments described below. It is well understood by those in the art who has the average knowledge on this field that the embodiments of the present invention are given to explain the present invention more precisely.

In addition, the "inclusion" of an element throughout the specification does not exclude other elements, but may include other elements, unless specifically stated otherwise.

In an aspect of the present invention, the present invention provides a pharmaceutical composition for preventing or treating cancer comprising a compound represented by formula 1 below, a stereoisomer thereof, a solvate thereof, a hydrate thereof, or a pharmaceutically acceptable salt thereof as an active ingredient.

[Formula 1]

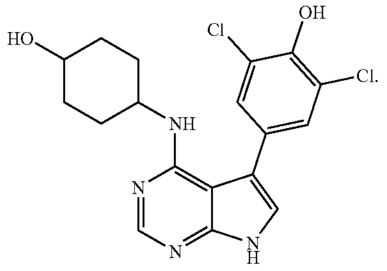

In another aspect of the present invention, the compound represented by formula 1 above can be (trans)-2,6-dichloro-4-(4-(4-hydroxycyclohexylamino)-7H-pyrrolo[2,3-D]pyrimidin-5-yl) phenol.

In another aspect of the present invention, the pharmaceutical composition can be used in combination treatment with radiation or anticancer agents.

The anticancer agent can be at least one selected from the group consisting of cisplatin, sorafenib, OKN-007, gefitinib, doxorubicin, vinblastine, taxol, etoposide, 5-FU, and ifosfamide.

In another aspect of the present invention, the pharmaceutical composition can enhance immunity. In Example 10 below, immune cell changes in the tumor microenvironment were evaluated. As a result, it was confirmed that when the compound of Example 1 was administered alone or in combination with radiation, the proportion of CD8 positive T cells was increased, M1 TAM was increased, and M2 TAM was decreased.

In the present invention, the term "pharmaceutically acceptable salt" refers to salts commonly used in the pharmaceutical industry, for example, inorganic ionic salt made from calcium, potassium, sodium and magnesium; inorganic acid salts made from hydrochloric acid, nitric acid, phosphoric acid, bromic acid, iodic acid, perchloric acid, and sulfuric acid; organic acid salts made from acetic acid, trifluoroacetic, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc.; sulfonic acid salts made from methanesulfonic acid, ethanesulfonic acid, benzenesulfonic acid, p-toluenesulfonic acid, and naphthalenesulfonic acid; amino acid salts made from glycine, arginine, lysine, etc.; and amine salts made from trimethylamine, triethylamine, ammonia, pyridine, picoline, etc., but these salts do not limit the types of salts of the present invention.

In the present invention, the term "isomer" refers to a compound of the present invention or a salt thereof that has the same chemical formula or molecular formula but is structurally or sterically different. The isomer includes structural isomers such as tautomers and stereoisomers, and stereoisomers include both R or S isomers with asymmetric carbon centers (optical isomers, enantiomers) and geometric isomers (trans, cis). In the present invention, all stereoisomers of the compound represented by formula 1 and mixtures thereof are also included in the scope of the present invention.

In the present invention, the term "hydrate" refers to a compound represented by formula 1 above and water bound by non-covalent intermolecular forces, and may include a stoichiometric or non-stoichiometric amount of water. Specifically, the hydrate may contain water in a ratio of about 0.25 mole to about 10 mole based on 1 mole of the active ingredient, and more specifically may contain about 0.5 mole, about 1 mole, about 1.5 mole, about 2 mole, about 2.5 mole, about 3 mole, about 5 mole, etc.

In the present invention, the term "solvate" refers to a compound represented by formula 1 above and a solvent other than water bound by non-covalent intermolecular forces, and may include a stoichiometric or non-stoichiometric amount of water. Preferred solvents are volatile, non-toxic, and can be administered to humans in trace amounts. Specifically, the solvate may contain water in a ratio of about 0.25 mole to about 10 mole based on 1 mole of the active ingredient, and more specifically may contain about 0.5 mole, about 1 mole, about 1.5 mole, about 2 mole, about 3 mole, about 5 mole, etc.

In the present invention, the term "about" refers to a numerical value that is ±10% of the preceding value.

In the present invention, the term "comprising as an active ingredient" means containing in a dosage range that brings the effect of preventing, ameliorating, or treating cancer, and the dosage range may vary depending on the severity and formulation, and the number of applications may also vary depending on the age, weight, and physical constitution of the subject. In one embodiment of the present invention, in the pharmaceutical composition of the present invention, the compound represented by formula 1 is included, for example, in an amount of 0.001 mg/kg or more, preferably 0.1 mg/kg or more, more preferably 10 mg/kg or more, more preferably 100 mg/kg or more, more preferably 250 mg/kg or more, and most preferably 0.1 g/kg or more. The quantitative upper limit of the compounds represented by formula 1 included in the pharmaceutical composition of the present invention may be selected by those skilled in the art within an appropriate range.

The pharmaceutical composition according to the present invention may comprise an effective amount of the compound represented by formula 1 alone or may include one or more pharmaceutically acceptable carriers, excipients or diluents.

The pharmaceutically acceptable carrier, excipient, or diluent refers to a substance that is physiologically acceptable and does not typically cause gastrointestinal upset, allergic reactions such as dizziness, or similar reactions when administered to humans. Examples of the carriers, excipients and diluents include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oil, but not always limited thereto. In addition, fillers, anticoagulants, lubricants, wetting agents, fragrances, emulsifiers and preservatives may be additionally included.

The pharmaceutical composition of the present invention can be formulated using the methods known in the art to provide rapid, sustained or delayed release of the active ingredient after administration to a subject. The pharmaceutical composition can be formulated in the form of an oral preparation, an injectable preparation, or an external preparation. The oral preparation can be selected from the group consisting of tablets, pills, powders, granules, capsules, suspensions, solutions, emulsions, syrups and freeze-dried preparations, but not always limited thereto. In addition, the external preparation can be selected from the group consisting of creams, gels, ointments, emulsions, suspensions, sprays, and transdermal patches, but not always limited thereto.

The pharmaceutical composition of the present invention can be administered through various routes, including oral administration, transdermal administration, subcutaneous administration, intravenous administration, or intramuscular administration.

In the present invention, the term "amelioration" refers to alleviation, prevention, or treatment of cancer symptoms by administering, ingesting, or applying the pharmaceutical composition or food composition of the present invention to a subject suffering from cancer.

In the present invention, the term "prevention" refers to inhibiting or blocking cancer symptoms by administering, ingesting, or applying the pharmaceutical composition or food composition of the present invention to a subject not suffering from cancer.

In the present invention, the term "treatment" refers to complete cure of cancer symptoms as well as partial cure, improvement, and alleviation of cancer symptoms as a result of administering the pharmaceutical composition of the present invention to a subject suffering from cancer.

In the present invention, the term 'subject' refers to any animal, including humans, which has already developed or may develop cancer.

The pharmaceutical composition of the present invention is administered in a pharmaceutically effective amount.

In the present invention, the term "pharmaceutically effective amount" means an amount sufficient to treat a disease with a reasonable benefit/risk ratio applicable to medical treatment or improvement. The effective dose level depends on the factors including subject type and severity, age, gender, drug activity, sensitivity to drug, time of administration, administration route and excretion rate, duration of treatment, concomitant drugs, and other factors well known in the medical field.

In the present invention, the term "administration" means to provide a substance to a subject or patient by any appropriate method. The substance can be administered parenterally (e.g., intravenous injection, subcutaneous injection, intraperitoneal injection, or topical injection) or administered orally according to the desired method. The dosage range varies depending on the patient's weight, age, gender, health condition, diet, administration time, administration method, excretion rate, and severity of the disease. Specifically, in the present invention, the term "parenteral administration" refers to a method of administration subcutaneously, intramuscularly, intravenously, or intraperitoneally using a tube, excluding oral administration. In addition, in the present invention, the term "oral administration" refers to an administration method of injecting an agent for ameliorating pathological symptoms into the mouth.

For formulations for parenteral administration, sterilized suspensions, liquids, water-insoluble excipients, suspensions, emulsions, eye drops, ophthalmic ointments, syrups, suppositories, external preparations such as aerosols and sterilized injections can be prepared by the conventional method, and preferably pharmaceutical compositions of creams, gels, patches, sprays, ointments, plasters, lotions, liniments, ophthalmic ointments, eye drops, pastes or cataplasms can be prepared, but not always limited thereto. Water-insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

In the present invention, the cancer can be anyone selected from the group consisting of lung cancer, non-small cell lung cancer (NSCL), bronchial alveolar cell lung cancer, ovarian cancer, colorectal cancer, melanoma, stomach cancer, gastrointestinal cancer, liver cancer, bone cancer, pancreatic cancer, skin cancer, head and neck cancer, skin or eye melanoma, uterine cancer, rectal cancer, colon cancer, breast cancer, uterine sarcoma, fallopian tube carcinoma, endometrial carcinoma, cervical carcinoma, vaginal carcinoma, vulvar carcinoma, esophageal cancer, laryngeal cancer, small intestine cancer, thyroid cancer, parathyroid cancer, soft tissue sarcoma, urethral cancer, penile cancer, prostate cancer, multiple myeloma, and chronic or acute leukemia, and preferably the cancer can be liver cancer, lung cancer, ovarian cancer, colorectal cancer, melanoma, or breast cancer.

In another aspect of the present invention, the present invention provides a health functional food composition for preventing or ameliorating cancer comprising a compound represented by formula 1 below, a stereoisomer thereof, a solvate thereof, a hydrate thereof, or a pharmaceutically acceptable salt thereof as an active ingredient.

[Formula 1]

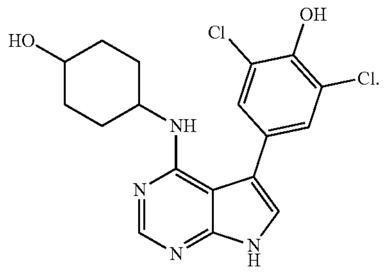

The food composition according to the present invention can be formulated in the same way as the pharmaceutical composition and used as a functional food or added to various foods. Food to which the food composition of the present invention can be added is exemplified by beverages, alcoholic beverages, confectionery, diet bars, dairy products, meat, chocolate, pizza, ramen, other noodles, gum, ice cream, and hangover relievers (drinks, low-viscosity gel type, pills, tablets, capsules, etc.), vitamin complexes, health supplements, etc.

The food composition of the present invention may include a compound represented by formula 1, a pharmaceutically acceptable salt thereof, a hydrate thereof, or a solvate thereof as an active ingredient, as well as ingredients commonly added during food production, for example, proteins, carbohydrates, fats, nutrients, seasonings and flavoring agents. Examples of the above-mentioned carbohydrates include monosaccharides such as glucose, fructose, etc.; disaccharides such as maltose, sucrose, oligosaccharides, etc.; and polysaccharides such as common sugars including dextrin and cyclodextrin, and sugar alcohols such as xylitol, sorbitol, and erythritol. Natural sweetening agents (thaumatin, stevia extract, for example rebaudioside A, glycyrrhizin, etc.) and synthetic sweetening agents (saccharin, aspartame, etc.) can be included as a sweetening agent. When the food composition of the invention is formulated as drinks and beverages, it may additionally include citric acid, high fructose corn syrup, sugar, glucose, acetic acid, malic acid, fruit juice, and various plant extracts in addition to a compound represented by formula 1 or 2, a pharmaceutically acceptable salt thereof, a hydrate thereof or a solvate thereof.

The present invention provides a health functional food or health supplement food containing the food composition comprising a compound represented by formula 1, a pharmaceutically acceptable salt thereof, a hydrate thereof, or a solvate thereof as an active ingredient. In the present invention, the term "health functional food or health supplement food" refers to a food manufactured and processed using raw materials or ingredients that have functional properties useful to the human body in accordance with the Act on Health Functional Food. The term "functional" food refers to a food consumed for the purpose of obtaining useful health effects such as regulating nutrients for the structure and function of the human body or physiological effects. In the present invention, the functional food is a food product prepared by adding a compound represented by formula 1, a pharmaceutically acceptable salt thereof, a hydrate thereof, or a solvate thereof to food materials such as beverages, teas, spices, gum, and confectionery, or by encapsulating, powdering, or suspending. The above functional food has specific health effects when consumed, but unlike general drugs, it has the advantage of not having any side effects that may occur when taking the drug for a long time because it is manufactured using food as a raw material. The health functional food or health supplement food of the present invention obtained in this way is very useful because it can be taken on a daily basis. The amount of a compound represented by formula 1, a pharmaceutically acceptable salt thereof, a hydrate thereof, or a solvate thereof in such a health functional food or health supplement food cannot be uniformly prescribed because it depends on the type of the health functional food being targeted, but it can be added in a range that does not impair the original taste of the food, and is generally in the range of 0.01 to 50 wt %, preferably 0.1 to 20 wt % of the target food. In addition, in the case of the health functional food or health supplement food in the form of pills, granules, tablets, or capsules, it is usually added in the range of 0.1 to 100 wt %, preferably 0.5 to 80 wt %. In one embodiment of the present invention, the health functional food or health supplement food of the present invention may be in the form of a pill, tablet, capsule, or beverage.

The food composition of the present invention can contain a conventional food additive. The suitability as a 'food additive' is determined by the standards and criteria for the item in question in accordance with the general rules and general test methods for food additives approved by the Ministry of Food and Drug Safety, unless otherwise specified.

The items listed in the "Korean Food Additives Code" include, for example, chemical compounds such as ketones, glycine, potassium citrate, nicotinic acid, and cinnamic acid; natural additives such as persimmon color, licorice extract, crystalline cellulose, sorghum color, and guar gum; and mixed preparations such as sodium L-glutamate preparations, alkali agents for noodles, preservative formulations, and tar color formulations.

In addition, the food composition of the present invention can be prepared and processed in the form of tablets, capsules, powders, granules, liquids, pills, and the like, for the purpose of preventing and/or ameliorating cancer.

For example, the health functional food in tablet form can be prepared by granulating a mixture of a food composition comprising a compound represented by formula 1, a pharmaceutically acceptable salt thereof, a hydrate thereof, or a solvate thereof as an active ingredient, an excipient, a binder, a disintegrant, and other additives in a conventional manner, and then compression molding the mixture with a lubricant or the like, or directly compression molding the mixture. In addition, the health functional food in tablet form can contain a flavors enhancer or the like as needed, and can also be coated with a suitable coating agent as needed.

Among the health functional food in capsule form, hard capsules can be prepared by filling conventional hard capsules with a mixture of a food composition comprising a compound represented by formula 1, a pharmaceutically acceptable salt thereof, a hydrate thereof, or a solvate thereof as an active ingredient, and additives such as excipients, or a granularity thereof or a coated granularity thereof. Soft capsules can be prepared by filling a mixture of a food composition comprising a compound represented by formula 1, a pharmaceutically acceptable salt thereof, a hydrate thereof, or a solvate thereof as an active ingredient, and additives such as excipients into a capsule base such as gelatin. The soft capsules can contain plasticizers such as glycerin or sorbitol, colorants, preservatives, etc., if necessary.

The health functional food in pill form can be prepared by molding a mixture of a food composition comprising a compound represented by formula 1, a pharmaceutically acceptable salt thereof, a hydrate thereof, or a solvate thereof as an active ingredient, an excipient, a binder, a disintegrant, and the like in any suitable manner, and if necessary, it can be coated with white sugar or another suitable coating agent, or coated with starch, talc, or other suitable substances.

The health functional food in granule form can be prepared by using a mixture of a food composition comprising a compound represented by formula 1, a pharmaceutically acceptable salt thereof, a hydrate thereof, or a solvate thereof as an active ingredient, an excipient, a binder, a disintegrant, and the like in any suitable manner, and if necessary, it can contain flavoring agents, flavors enhancers, etc. When a particle size test was conducted using No. 12 (1680 μm), No. 14 (1410 μm), and No. 45 (350 μm) sieves, the entire amount of health functional food in granule form passed through the No. 12 sieve, less than 5.0% of the total amount remained in the No. 14 sieve, and less than 15.0% of the total amount passed through the No. 45 sieve.

There is no particular limitation on the type of food, and it includes all health functional foods in the conventional sense.

The matters mentioned in the pharmaceutical composition and food composition of the present invention are applied in the same manner unless they are mutually contradictory.

In another aspect of the present invention, the present invention provides a pharmaceutical kit for preventing or treating cancer comprising a first component containing a pharmaceutically effective amount of an anticancer agent; and a second component containing a compound represented by formula 1 below, a stereoisomer thereof, a solvate thereof, a hydrate thereof, or a pharmaceutically acceptable salt thereof as an active ingredient.

[Formula 1]

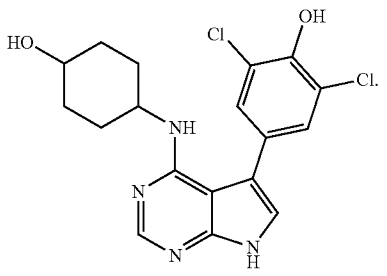

In another aspect of the present invention, the compound represented by formula 1 above can be (trans)-2,6-dichloro-4-(4-(4-hydroxycyclohexylamino)-7H-pyrrolo[2,3-D]pyrimidin-5-yl)phenol.

In another aspect of the present invention, the cancer can be anyone selected from the group consisting of lung cancer, non-small cell lung cancer (NSCL), bronchial alveolar cell lung cancer, ovarian cancer, colorectal cancer, melanoma, stomach cancer, gastrointestinal cancer, liver cancer, bone cancer, pancreatic cancer, skin cancer, head and neck cancer, skin or eye melanoma, uterine cancer, rectal cancer, colon cancer, breast cancer, uterine sarcoma, fallopian tube carcinoma, endometrial carcinoma, cervical carcinoma, vaginal carcinoma, vulvar carcinoma, esophageal cancer, laryngeal cancer, small intestine cancer, thyroid cancer, parathyroid cancer, soft tissue sarcoma, urethral cancer, penile cancer, prostate cancer, multiple myeloma, and chronic or acute leukemia.

In another aspect of the present invention, the anticancer agent can be at least one selected from the group consisting of cisplatin, sorafenib, OKN-007, gefitinib, doxorubicin, vinblastine, taxol, etoposide, 5-FU, and ifosfamide.

In another aspect of the present invention, the present invention provides a method for preventing or treating cancer, comprising a step of administering a compound represented by formula 1 described herein, a stereoisomer thereof, a solvate thereof, a hydrate thereof, or a pharmaceutically acceptable salt thereof to a subject in need thereof.

In another aspect of the present invention, the present invention provides a method for preventing or treating cancer, comprising a step of co-administering a compound represented by formula 1 described herein, a stereoisomer thereof, a solvate thereof, a hydrate thereof, or a pharmaceutically acceptable salt thereof and radiation or anticancer agent to a subject in need thereof.

In another aspect of the present invention, the present invention provides a use of a compound represented by formula 1 described herein, a stereoisomer thereof, a solvate thereof, a hydrate thereof, or a pharmaceutically acceptable salt thereof for the preparation of a medicament for use in the prevention or treatment of cancer.

In another aspect of the present invention, the present invention provides a use of a compound represented by formula 1 described herein, a stereoisomer thereof, a solvate thereof, a hydrate thereof, or a pharmaceutically acceptable salt thereof and radiation or anticancer agent, which are administered in combination, for the preparation of a medicament for use in the prevention or treatment of cancer.

For the above method or use, the detailed description of the pharmaceutical composition described above may be applied.

Hereinafter, the present invention will be described in detail by the following examples and experimental examples.

However, the following examples and experimental examples are only for illustrating the present invention, and the contents of the present invention are not limited thereto.

EXAMPLES

Example 1: Preparation of (trans)-2,6-dichloro-4-(4-(4-hydroxycyclohexylamino)-7H-pyrrolo[2,3-d]pyrimidin-5-yl)phenol

[Reaction Formula 1]

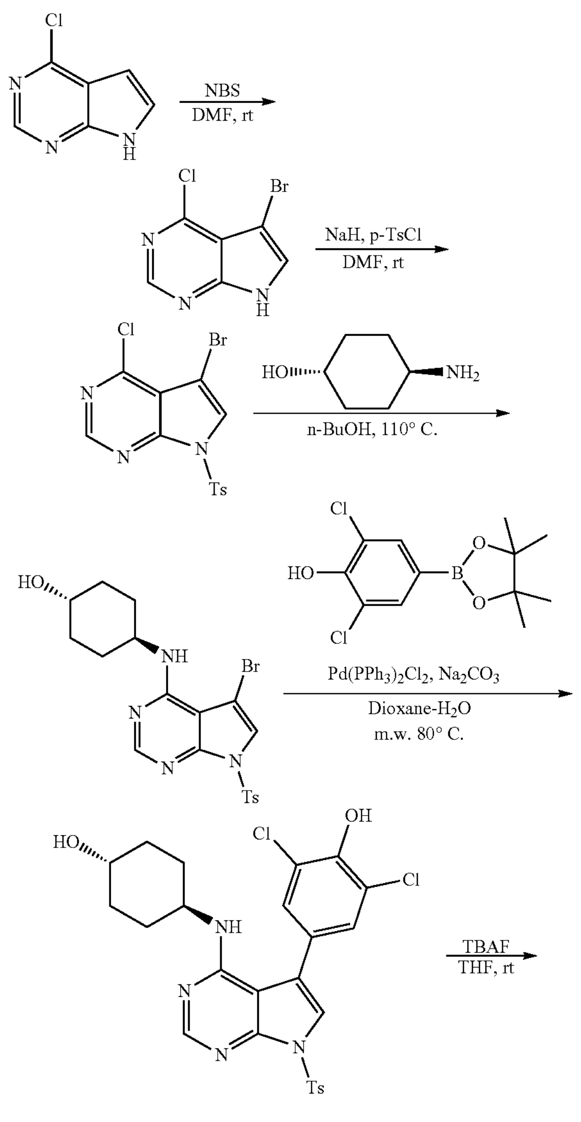

-continued

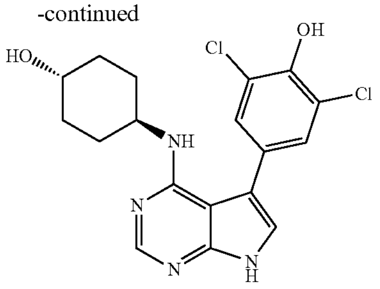

Step 1

DMF (30 mL) was added to 4-chloro-7H-pyrrolo[2,3-d]pyrimidine (2 g, 13.02 mmol), and NBS (2.52 g, 14.24 mmol) was added thereto at 0° C. The mixture was stirred at room temperature for 3 hours. Upon completion of the reaction, the solvent was removed under high pressure, and the resultant was mixed with water, filtered, washed with hexane, and dried to give 5-bromo-4-chloro-7H-pyrrolo[2,3-d]pyrimidine (2.66 g, 88%).

$^{1}H$ NMR (DMSO, 300 MHz): δ 7.81 (s, 1H), 8.76 (s, 1H), 5.02 (br s, 1H).

Step 2

NaH (0.41 g, 10.3 mmol) was added to 5-bromo-4-chloro-7H-pyrrolo[2,3-d]pyrimidine (1.2 g, 5.16 mmol) dissolved in DMF (10 mL), followed by stirring at 0° ° C. for 30 minutes. After adding p-tosyl chloride (1.36 g, 7.16 mmol), the mixture was stirred at room temperature for 6 hours. Upon completion of the reaction, water was added thereto, stirred for 10 minutes, and the resultant was collected by filtration, and dried to give 5-bromo-4-chloro-7-tosyl-7H-pyrrolo[2,3-d]pyrimidine (1.79 g, 90%).

$^{1}H$ NMR ($CDCl_3$, 300 MHz): δ 8.76 (s, 1H), 8.09 (d, 2H, J=8.1 Hz), 7.54 (s, 1H), 7.34 (d, 2H, J=8.1 Hz), 2.41 (s, 3H).

Step 3

N-BuOH (10 mL) was added to 5-bromo-4-chloro-7-tosyl-7H-pyrrolo[2,3-d]pyrimidine (500 mg, 1.29 mmol), to which trans-4-aminocyclohexan-1-ol (223 mg, 1.94 mmol) and DIPEA (2.58 mmol) were added. The mixture was heated at 110° C. for 3 hours. The solvent was removed under high pressure, and the residue was purified by chromatography to give (trans)-4-((5-bromo-7-tosyl-7H-pyrrolo[2,3-d]pyrimidin-4-yl)amino)cyclohexan-1-ol (540 mg, 90%).

$^{1}H$ NMR ($CDCl_3$, 300 MHZ): δ 8.37 (s, 1H), 8.06 (d, 2H, J=8.3 Hz), 7.45 (s, 1H), 7.31 (d, 2H, J=8.2 Hz), 5.87 (d, 1H), 4.12 (m, 1H), 3.70 (m, 1H), 2.40 (s, 3H), 2.16 (m, 2H), 2.03 (m, 2H), 1.54 (m, 2H), 1.31 (m, 2H).

Step 4

(Trans)-4-((5-bromo-7-tosyl-7H-pyrrolo[2,3-d]pyrimidin-4-yl)amino)cyclohexan-1-ol (200 mg, 0.43 mmol), 2,6-dichloro-4-(4,4,5,5-tetramethyl-1,3,2-dioxabororene-2-yl) phenol (0.86 mmol), $Na_2CO_3$ (0.86 mmol), dioxane (4 mL) and water (1 mL) were placed in a microwave vial. The solvent was degassed for 15 minutes, $Pd(PPh_3)_2Cl_2$ (10 mol %) was added thereto, and irradiated by microwave at 80° C. for 30 minutes. The solution was filtered through a celite layer, the filtrate was washed with brine (10 mL×5), and the organic layer was concentrated and subjected to chromatography (10% methanol:dichloromethane) to give (trans)-2,6-dichloro-4-(4-((-4-hydroxycyclohexyl)amino)-7-tosyl-7H-pyrrolo[2,3-d]pyrimidin-5-yl)phenol (40%).

$^{1}H$ NMR ($CDCl_3$, 300 MHZ): δ 8.46 (s, 1H), 8.11 (d, 2H, J=8.36 Hz), 7.41 (s, 1H), 7.36 (s, 2H), 7.31 (d, 2H, J=8.13

Hz), 6.03 (m, 1H), 4.71 (d, 1H), 4.09 (m, 1H), 3.63 (m, 1H), 2.41 (s, 3H), 2.05 (m, 2H), 1.89 (m, 2H), 1.40 (m, 2H), 1.10 (m, 2H).

Step 5

1 M TBAF (in THF) was added to the above intermediate (trans)-2,6-dichloro-4-(4-((-4-hydroxycyclohexyl)amino)-7-tosyl-7H-pyrrolo[2,3-d]pyrimidin-5-yl)phenol and stirred at room temperature for 20 hours. The reactant was purified by chromatography (15% methanol:dichloromethane+0.1% aqueous ammonia) under reduced pressure to give the title compound (40%).

$^1$H NMR (DMSO-d6, 300 MHz): δ 11.82 (br s, 1H), 10.16 (br s, 1H), 8.17 (s, 1H), 7.42 (s, 2H), 7.29 (s, 1H), 5.27 (d, 1H), 4.54 (m, 1H), 4.01 (m, 1H), 3.43 (m, 1H), 1.95 (m, 2H), 1.76 (m, 2H), 1.40 (m, 2H), 1.20 (m, 4H).

Example 2: Evaluation of Inhibition of Major Protein Expression

An experiment was performed to confirm the inhibitory effect of the compound of Example 1, the active ingredient of the pharmaceutical composition of the present invention, on the expression of major proteins on cancer cell growth through Western blotting.

Specifically, MDA-MB-231 cells, a TNBC cell line, were cultured in a 37° C., 5% $CO_2$ incubator, and the medium used for cell culture was RPMI-1640 supplemented with 10% FBS. Tumors were induced by subcutaneously injecting $5\times10^6$/head/100 µl of MDA-MB-231 cells into the right neck of BALB/c-nude mice (5 mice each in control and administration groups), and the experiment was performed when the tumor size reached 200 $mm^3$. The compound of Example 1, the active ingredient of the pharmaceutical composition of the present invention, was administered once by intravenous injection at concentrations of 5, 10, and 20 mg/kg (T4, T5, and T6) and then euthanized using $CO_2$, and the resulting tumor tissues from the control and administration groups were taken and subjected to Western blotting. Proteins were isolated from the tumor tissues and the results of Western blotting were confirmed using BRD4, c-myc, PD-L1, and Actin antibodies, respectively.

When comparing the expression of BRD4, c-myc, and PD-L1 in the T4, 5, and 6 groups treated with the compound of Example 1, the active ingredient of the pharmaceutical composition of the present invention, with that in the untreated negative control (NC), it was confirmed that the expression of proteins important in cancer formation in the T4, 5, and 6 groups was reduced.

Example 3: Evaluation of Inhibition of Breast Cancer Cell Line

An experiment was performed to confirm the growth inhibitory effect of the compound of Example 1, the active ingredient of the pharmaceutical composition of the present invention, on breast cancer cell lines through cell viability assay.

Specifically, the cell viability assay was performed as follows. BT20, a human-derived breast cancer cell line, and MDA-MB-231, a TNBC cell line, were each seeded in 96-well plates at the density of $5\times10^3$ cells/well and cultured for 24 hours. Then, I-bet 762 and the compound of Example 1 were treated thereto at different concentrations and cultured for 48 hours. At the end of the culture, 100 µl of WST-8 solution was added to each well of the plate, and the absorbance was measured with a microplate reader using a 450 nm optical filter to measure the formazan produced by the reducing factors in living cells.

As shown in FIGS. 2A-2B and 3A-3B, as a result of analyzing the formation of mammospheres by culturing the human-derived breast cancer cell line BT20 and the TNBC cell line MDA-MB-231, it was confirmed that the compound of Example 1, the active ingredient of the pharmaceutical composition of the present invention, inhibited the cell viability not only in a general breast cancer cell line, but also in a TNBC cell line dose dependently.

Figure 4A:
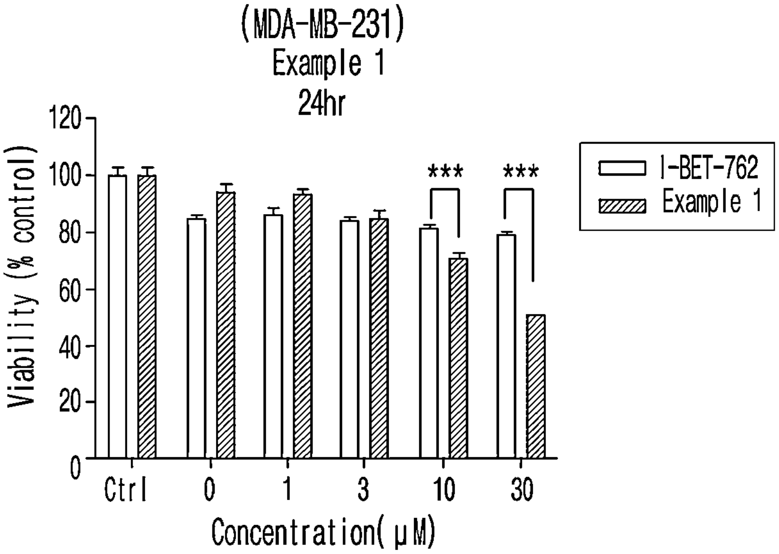
FIGS. 4A-4C are graphs showing the cell viability of MDA-MB-231, MDA-MB-453, and BT-20 after 24 hours of treatment with the compound of Example 1.
Figure 4B:
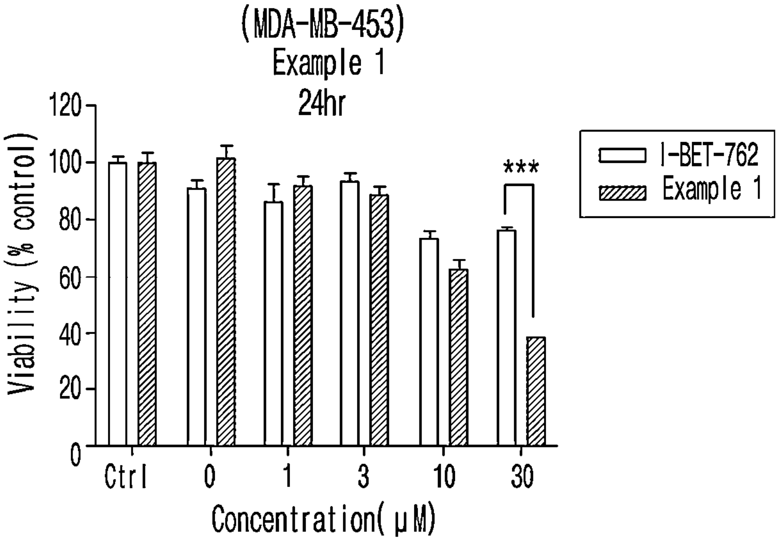
Figure 4C:
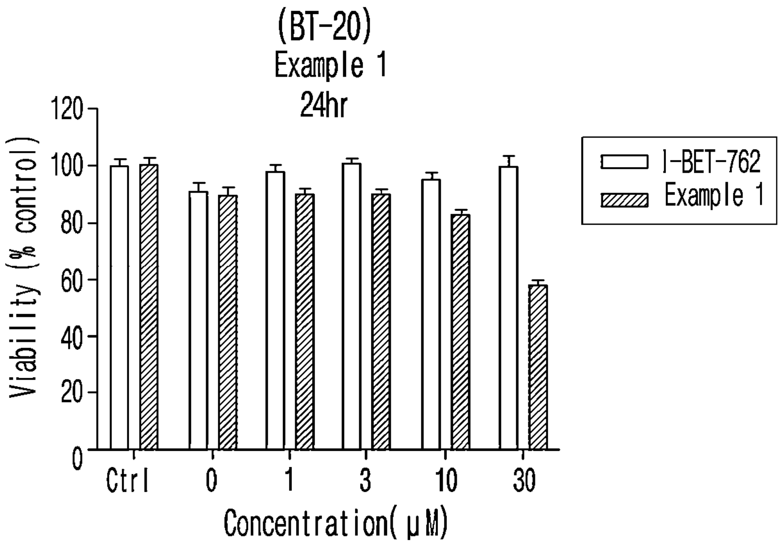

FIGS. 4A-4C show the cell viability of MDA-MB-231, MDA-MB-453, and BT-20 after 24 hours of treatment with the compound of Example 1. As shown in FIGS. 4A-4C, it was confirmed that the cell viability was suppressed not only in general breast cancer cell lines, but also in TNBC cell lines dose dependently.

Example 4: Evaluation of Breast Cancer Growth Inhibition

An experiment was performed to confirm the tumor inhibition of the compound of Example 1, the active ingredient of the pharmaceutical composition of the present invention, on a xenograft tumor sample of breast cancer cells (MBA-MB-231), a human-derived TNBC cell line.

Specifically, to confirm the in vitro inhibitory effect of the compound of Example 1, the active ingredient of the pharmaceutical composition of the present invention, on breast cancer cell viability, an experiment was performed using 80 female 5-week-old xenograft Balb/c nude mice, which were approximately 8 weeks old at the start of administration.

The experimental xenograft Balb/c nude mice lacks T cells, the immune cells, were selected as an animal model suitable for transplanting human cancer cells. At the time of administration, animals within ±20% of the total average body weight were selected, and tumor growth was checked twice a week on the surface, and the size of the tumor was measured with a vernier caliper for 3 weeks.

Figure 5:
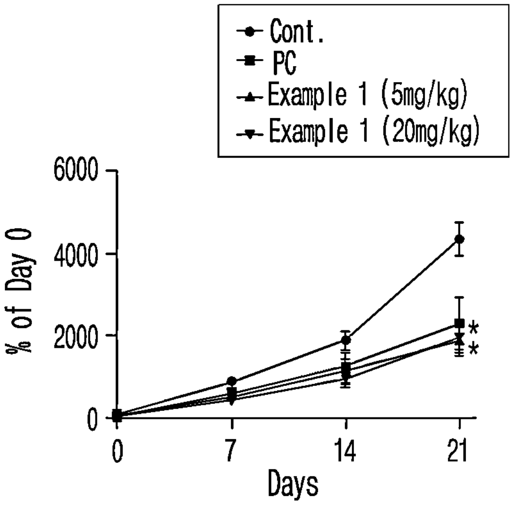
FIG. 5 is a graph confirming that the treatment with the compound of Example 1 can significantly inhibit tumor growth.

As shown in FIG. 5, it was confirmed that the compound of Example 1, the active ingredient of the pharmaceutical composition of the present invention, could significantly inhibit the tumor growth.

Example 5: Comparison of Apoptotic Body Frequency

An experiment was performed to confirm the tumor necrosis effect of the compound of Example 1, the active ingredient of the pharmaceutical composition of the present invention, by measuring the number of apoptotic bodies in tumors and H&E staining of the tumor tissues in BALB/c-nude mice injected with cancer cell lines.

Specifically, to measure the number of apoptotic bodies in the tumor tissues of the T4, T5, and T6 groups of Experimental Example 1, five areas where the tumor tissues were growing were randomly selected and the number of apoptotic bodies was measured at ×400 magnification. The sum of the measurements was calculated, expressed as individual values, and statistically compared using GraphPad Prism 5.

As a result of observing the apoptotic body, it was observed that the cells were shrunk and divided (blebs) and that empty space (hollow) surrounded the periphery. In addition, the eosinophilicity of the cytoplasm was increased, and the nucleus was small, concentrated or fragmented, and was observed to be phagocytosed by surrounding cells.

According to the measured number of apoptotic bodies in Table 1, the number was higher in the T4, T5, and T6 groups treated with the compound of Example 1, the active ingredient of the pharmaceutical composition of the present invention, compared to NC (Negative Control) dose dependently, confirming that the compound of Example 1 of the present invention had a tumor suppressive effect by increasing apoptosis of cancer cells.

Figure 6:
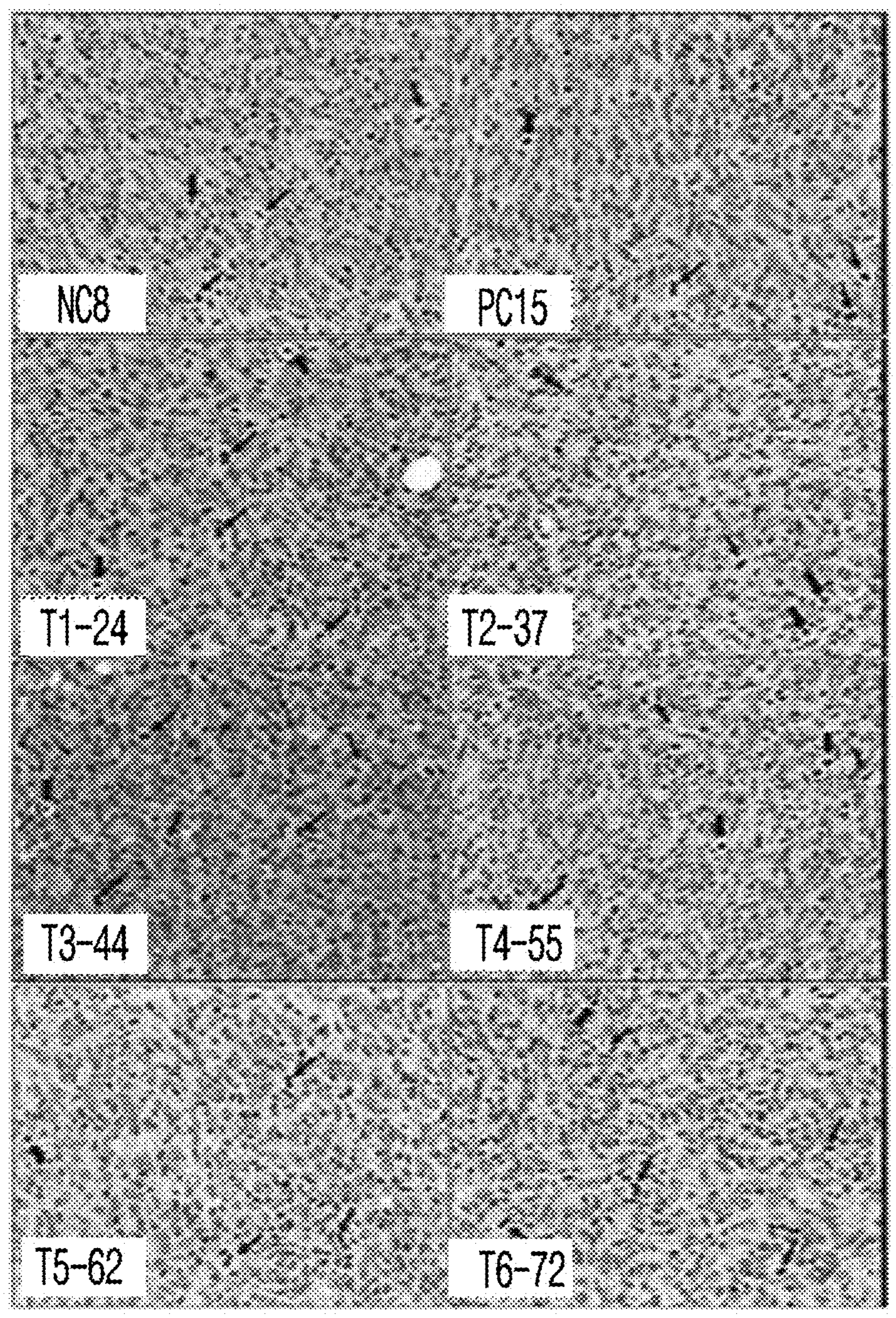
FIG. 6 is a set of photographs showing the apoptotic body that has undergone the apoptosis process.
Figure 7A:
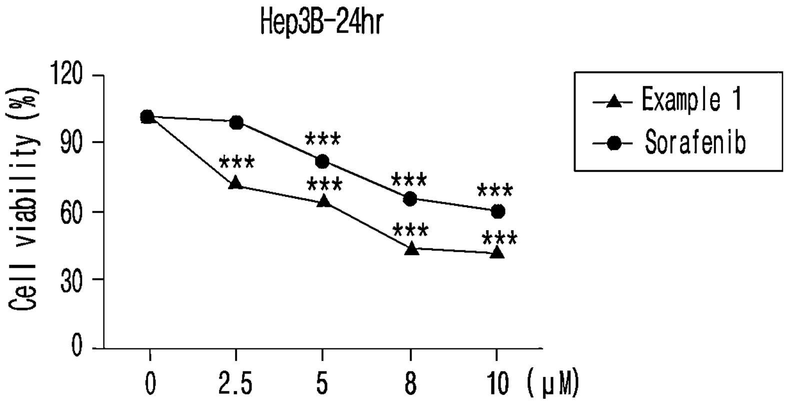
FIGS. 7A-7C are graphs showing the cell viability of Hep3B, a liver cancer cell line, after treatment with the compound of Example 1.
Figure 7B:
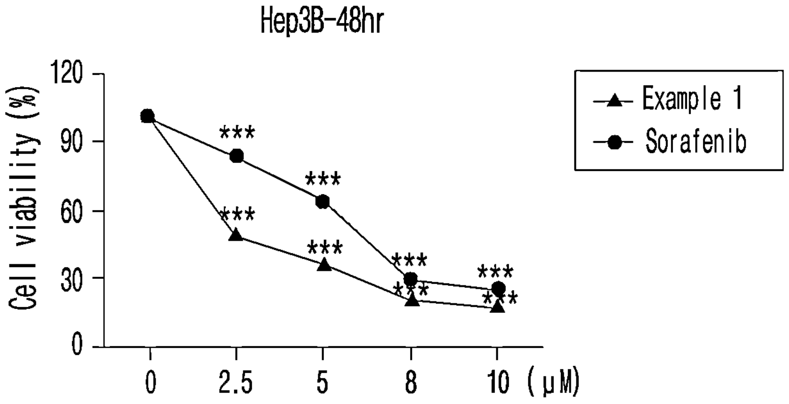
Figure 7C:
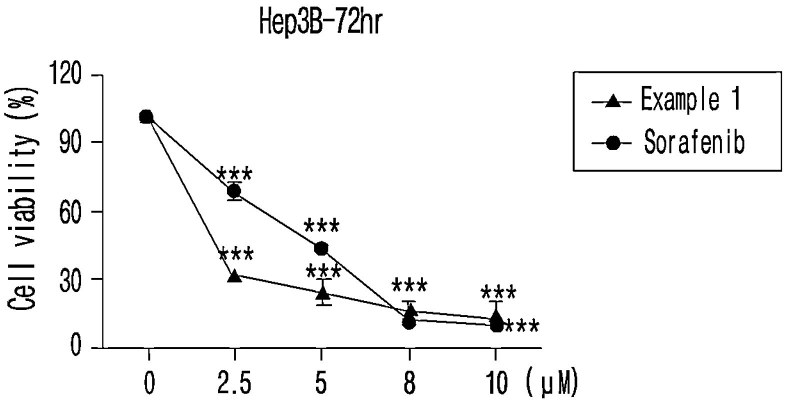
Figure 8A:
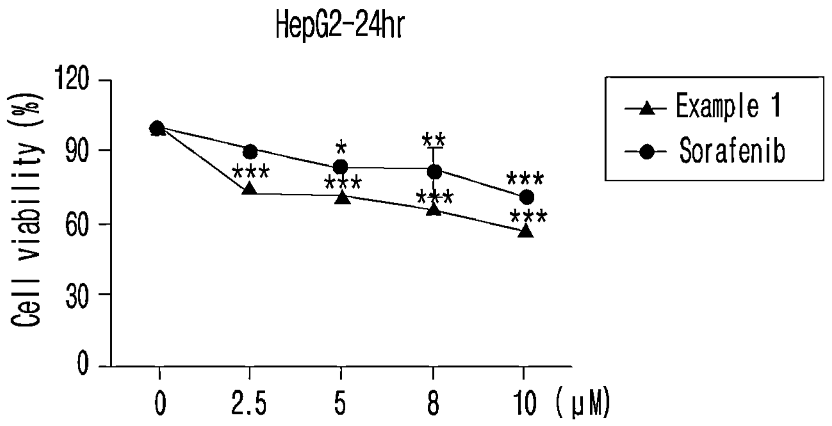
FIGS. 8A-8C are graphs showing the cell viability of HepG2, a liver cancer cell line, after treatment with the compound of Example 1.
Figure 8B:
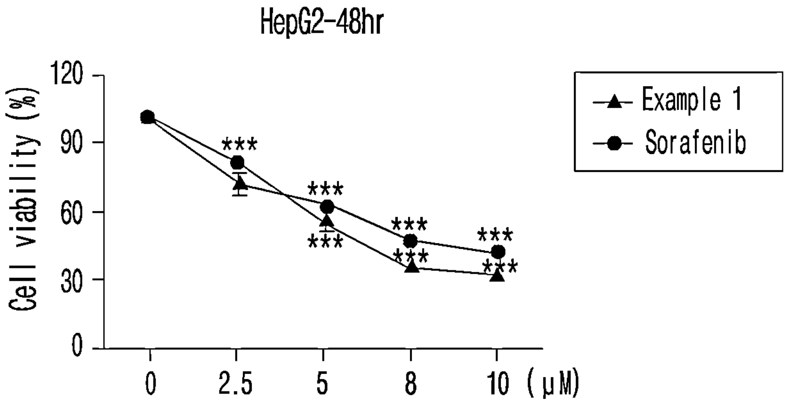
Figure 8C:
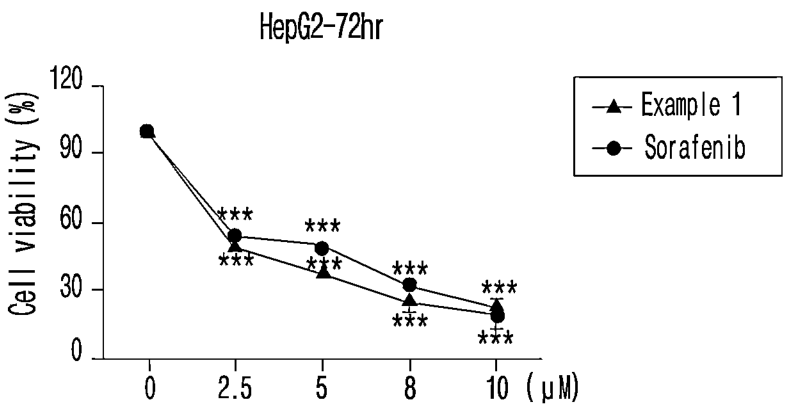

As shown in FIG. 6, the central area was cut out, a paraffin block was prepared through a general tissue processing process, and the tissue was sectioned at 3 μm thickness using a microtome. Then, the sections were stained with hematoxylin and eosin, and cell necrosis areas were observed.

When comparing the stained tissues of the NC group and the T4, T5, and T6 groups treated with the compound of Example 1, there were more areas of tissue necrosis in the group treated with the compound of Example 1, confirming that the compound of Example 1 caused necrosis of the tumor tissue and had a tumor suppressive effect.

TABLE 1

| | NC | PC | T4 | T5 | T6 |
|---|---|---|---|---|---|
| number of examined | 10 | 10 | 10 | 10 | 10 |
| number of apoptotic body | 7.2 ± 3.8 | 12.1 ± 5.4 | 9.6 ± 4.7 | 9.2 ± 4.6 | 13.6 ± 7.4 |

Example 6: Evaluation of Inhibition of Liver Cancer Cell Line

Whether the compound of Example 1, the active ingredient of the pharmaceutical composition of the present invention, has a growth inhibitory effect on cancer cell lines other than TNBC was confirmed.

Specifically, the WST-8 assay to check the cell viability of HepG2 and Hep3B, which are hepatocellular carcinoma cell lines shown in FIGS. 7A-7C and 8A-8C, was performed as follows. HepG2 and Hep3B were each seeded in 96-well plates at the density of 5×103 cells/well and cultured for 24 hours. Then, Sorafenib and OPT-0139 were diluted stepwise at a twofold concentration and then treated to the plates at different concentrations, followed by culture for 24, 48, and 72 hours. 100 μl of WST-8 solution was added to each well of the plate, and the absorbance was measured with a microplate reader using a 450 nm optical filter to measure the formazan produced by the reducing factors in living cells.

The cells that were not treated with Sorafenib and the compound of Example 1 showed a dark orange color, and the cells treated with Sorafenib and the compound of Example 1 showed a light pink color, which is the color of the culture medium of the cell line. Therefore, the number of living cells could be measured by measuring absorbance.

Figure 9:
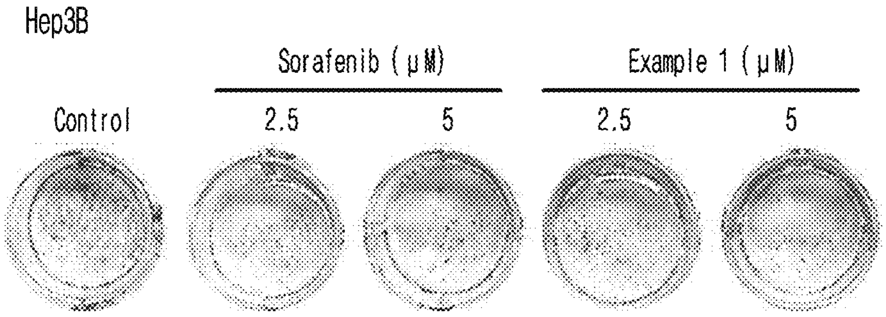
FIG. 9 is a set of photographs showing the results of treating Hep3B, a liver cancer cell line, with the compound of Example 1.
Figure 10:
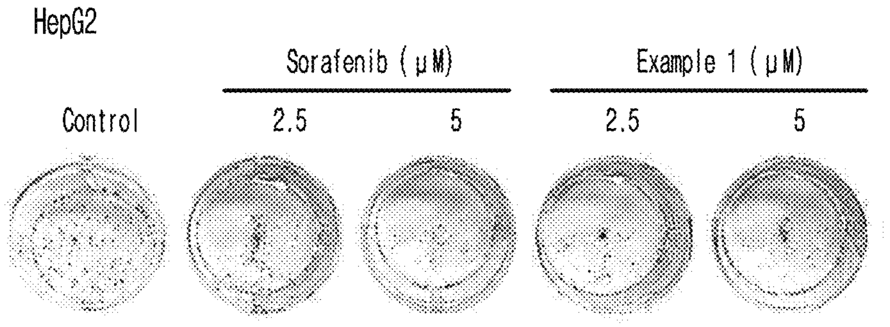
FIG. 10 is a set of photographs showing the results of treating HepG2, a liver cancer cell line, with the compound of Example 1.

As shown in FIGS. 9 and 10, the clonogenic assay was performed as follows. HepG2 and Hep3B were each seeded in 12-well plates at the density of $3\times10^3$ cells/well and cultured for 24 hours. Then, Sorafenib and the compound of Example 1 were treated thereto at 2.5 and 5 μM each and cultured for 10 days. Upon completion of the culture, the cells were washed with PBS, fixed with 37% formaldehyde, and stained with 0.01% crystal violet. After staining, the cells were washed with distilled water and the colonies of stained cells were photographed.

As a result of observing the colonies of stained cells, there was a clear difference in the number of colonies between the areas that were not treated with Sorafenib and the compound of Example 1 and the areas that were treated, showing the cell survival rate.

As shown in FIGS. 7A to 10, as a result of confirming the cell viability using WST-8 in the liver cancer cell lines Hep3B and HepG2 cells, it was found that the treatment of the compound of Example 1 and Sorafenib decreased the cell viability dose and time dependently, and showed a remarkable effect compared to Sorafenib, an existing targeted anticancer agent.

Example 7: Evaluation of Cytotoxicity on Various Cancer Cell Lines

The cytotoxicity of the compound of Example 1 against various cancer cell lines was evaluated through a process similar to the evaluation of liver cancer cell line inhibition described above. Etoposide, sold as an anticancer agent, was used as a control group drug.

Figure 11:
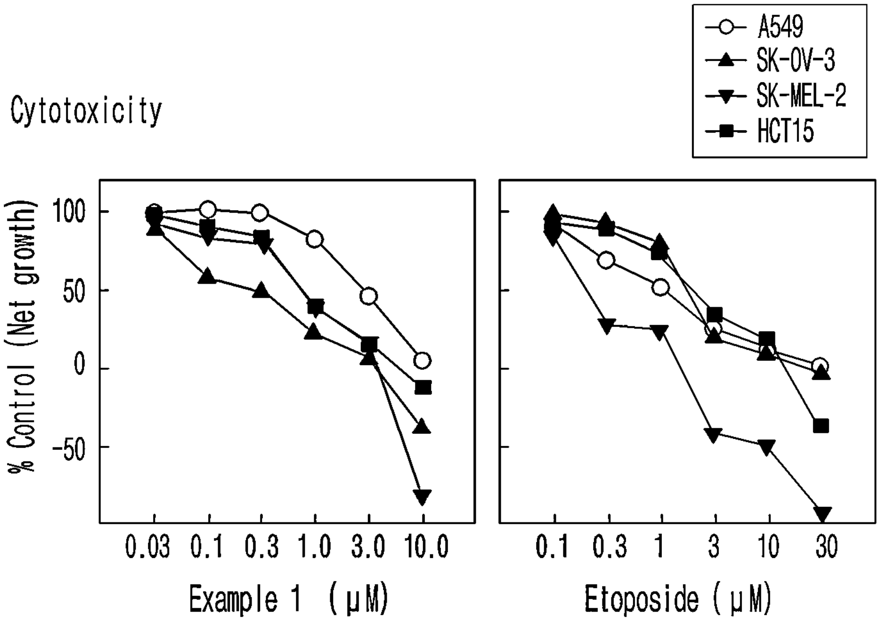
FIG. 11 is a set of graphs showing the results of confirming the toxicity of the compound of Example 1 of the present invention to various cancer cell lines.

The results are shown in FIG. 11.

FIG. 11 is a set of graphs showing the results of confirming the toxicity of the compound of Example 1 of the present invention to various cancer cell lines.

As shown in FIG. 11, the compound of Example 1 according to the present invention showed excellent toxicity to the cancer cell lines A549, SK-OV-3, SK-MEL-2, and HCT15 dose dependently, and thus it can be effectively used as an active ingredient in anticancer agents.

Example 8: Evaluation of Changes in Tumor Size According to Treatment Method in Triple-Negative Breast Cancer Allograft Mouse Model 4T1 murine triple negative breast cancer cells ($6\times10^5$ cells) were injected into the hind limbs of 6-week-old immune-competent BALB/c mice. Seven days after injection, after confirming consistent tumor growth, 10 mice from each group were selected and used in subsequent experiments.

The experimental groups consisted of a control group (no treatment), a radiotherapy group, a group treated with the compound of Example 1, and a group treated with a combination of the compound of Example 1 and radiotherapy. Each treatment was carried out for 31 days after tumor implantation.

Radiation treatment was performed using electron beams, and a total of 24 Gy was irradiated three times, once every two days for one week (Days 10, 12, and 14) (8 Gy×3). The compound of Example 1 was administered intravenously at a dose of 10 mg/kg once every 2 or 3 days (Days 10, 12, 14, 17, 19, and 21) for a total of 6 times over 2 weeks. On the days when radiation therapy and drug administration were conducted simultaneously, the compound of Example 1 was administered after confirming that the mice had recovered from anesthesia 4 hours after radiation therapy.

On each treatment day, the length and width of the tumor were measured using a vernier caliper, and then the tumor volume ($mm^3$) was calculated using mathematical formula 1 below.

$$\text{Volume (mm}^3\text{)}=\text{length (mm)}\times\{\text{width (mm)}\}^2\times0.5 \qquad \text{[Mathematical Formula 1]}$$

Figure 12:
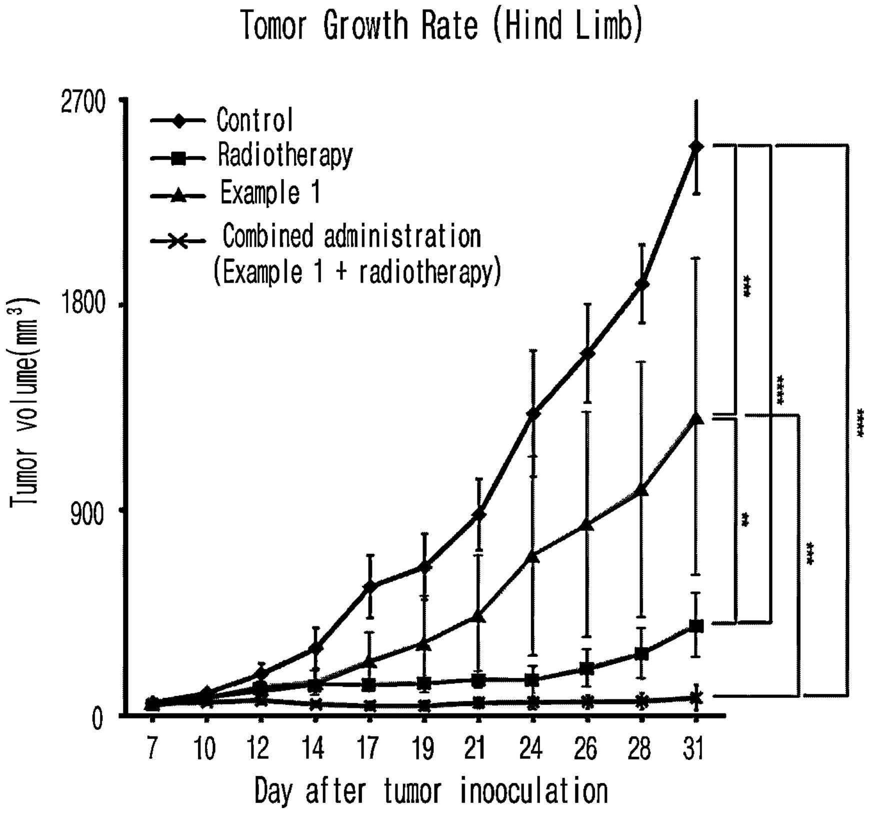
FIG. 12 is a graph showing the changes in tumor size according to treatment method in a triple-negative breast cancer allograft mouse model.

After injecting tumors into 10 mice for each treatment method in the same manner as above, the results of observing the tumor growth for 31 days are shown in FIG. 12. As a result, it was confirmed that administration of the compound of Example 1 alone significantly delayed the tumor growth compared to the control group. In addition, it was also confirmed that the combined administration of the compound of Example 1 and radiation had a superior inhibitory effect on the tumor growth compared to each administration alone.

Figure 13:
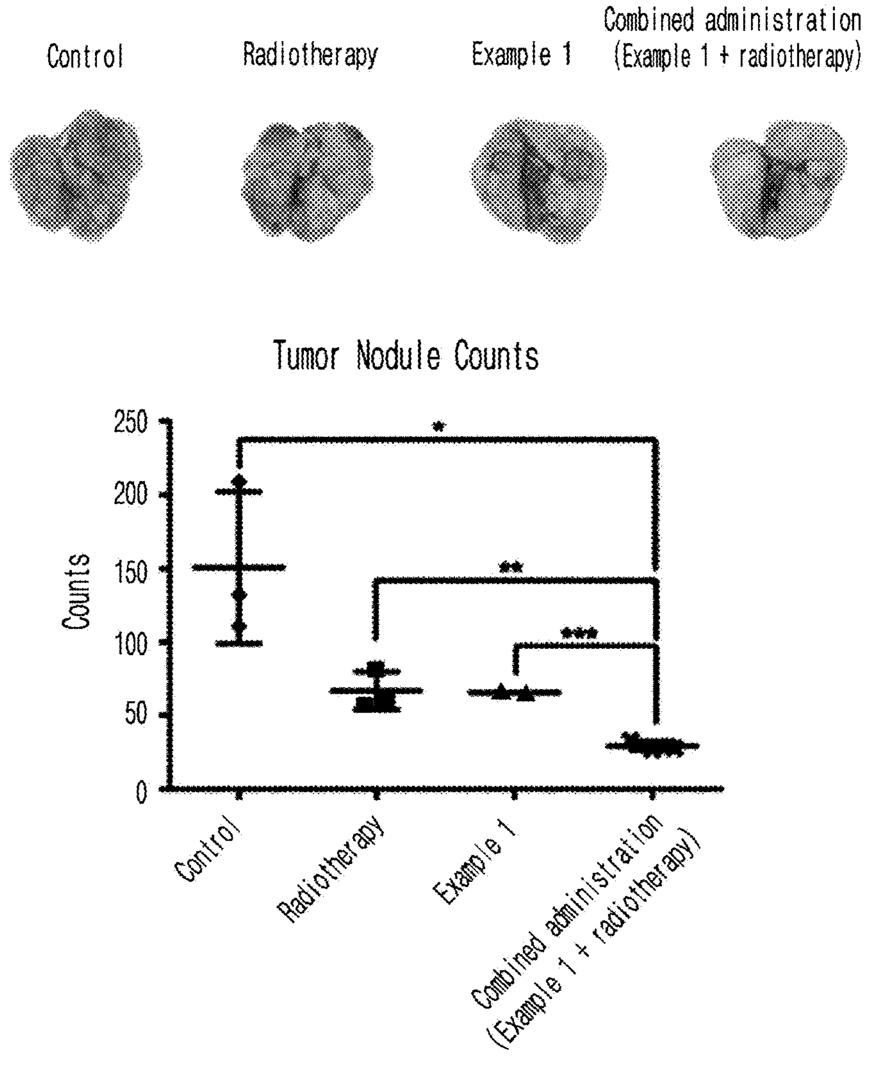
FIG. 13 is a set of photographs showing the lung and a graph showing the number of tumor nodules according to treatment method in a triple-negative breast cancer allograft mouse model.
Figure 14:
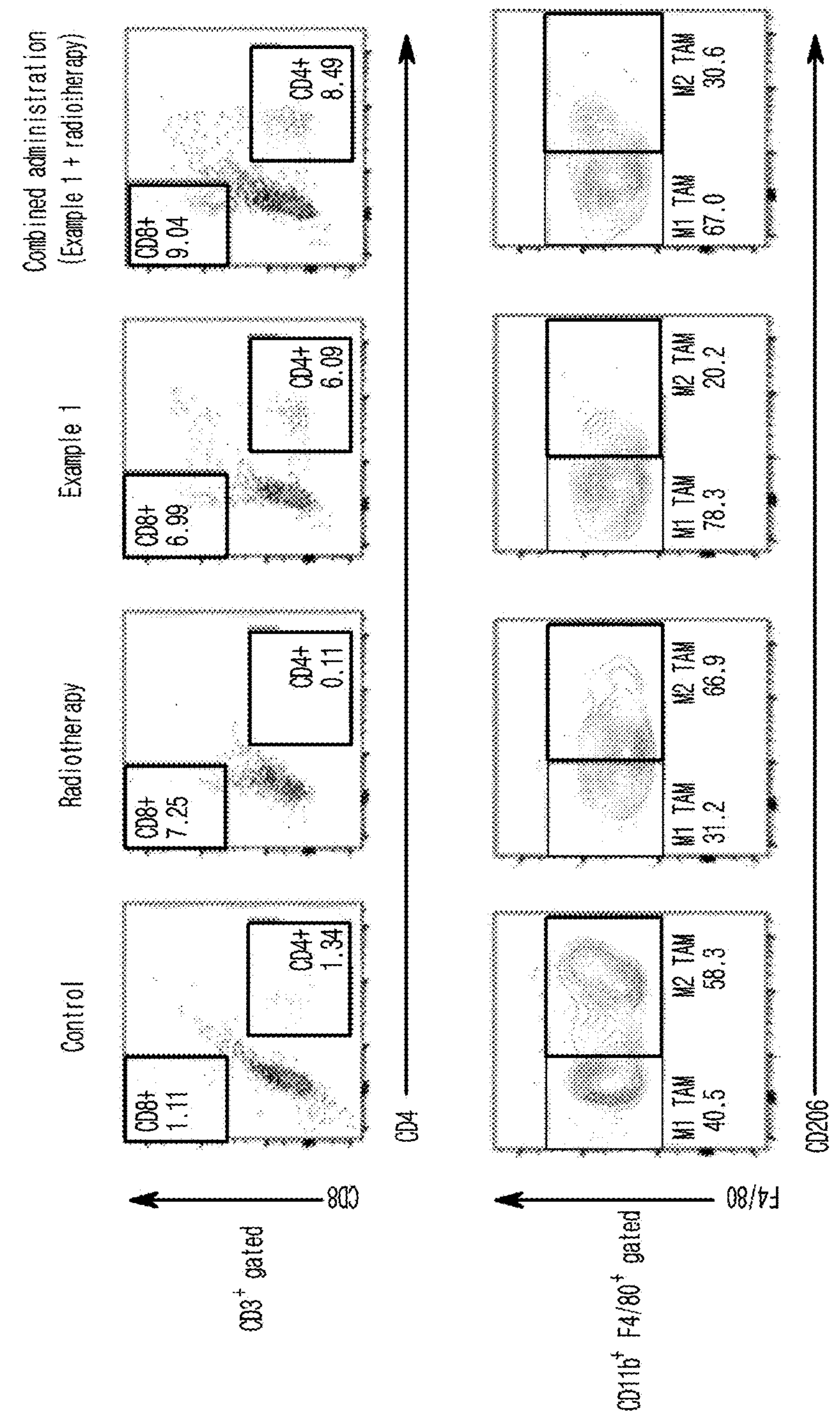
FIG. 14 is a set of graphs showing the results of observing the changes in immune cells according to treatment method in tumor cells through flow cytometry.
Figure 15A:
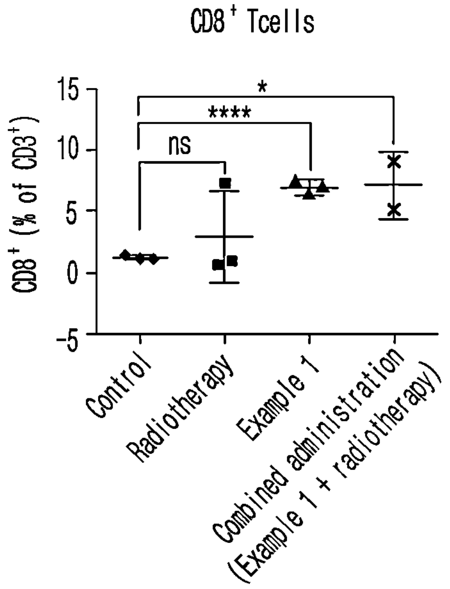
FIGS. 15A-15C are graphs showing the changes in immune cells according to treatment method in the tumor cells of FIG. 14 through flow cytometry.
Figure 15B:
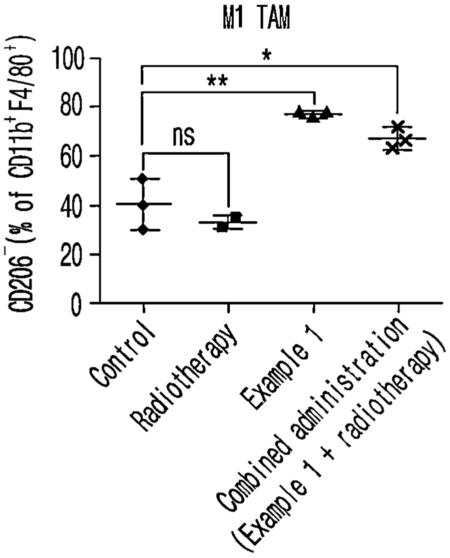
Figure 15C:
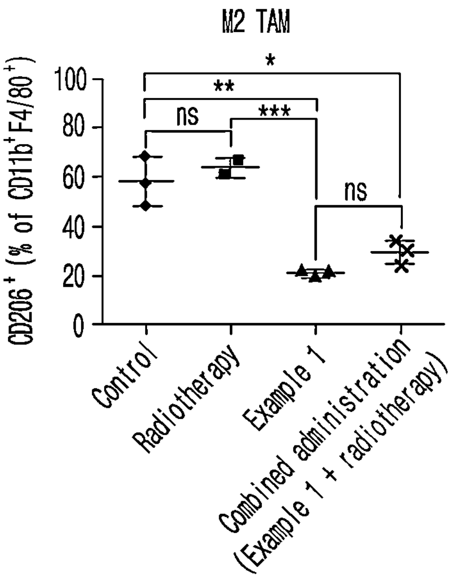
Figure 16:
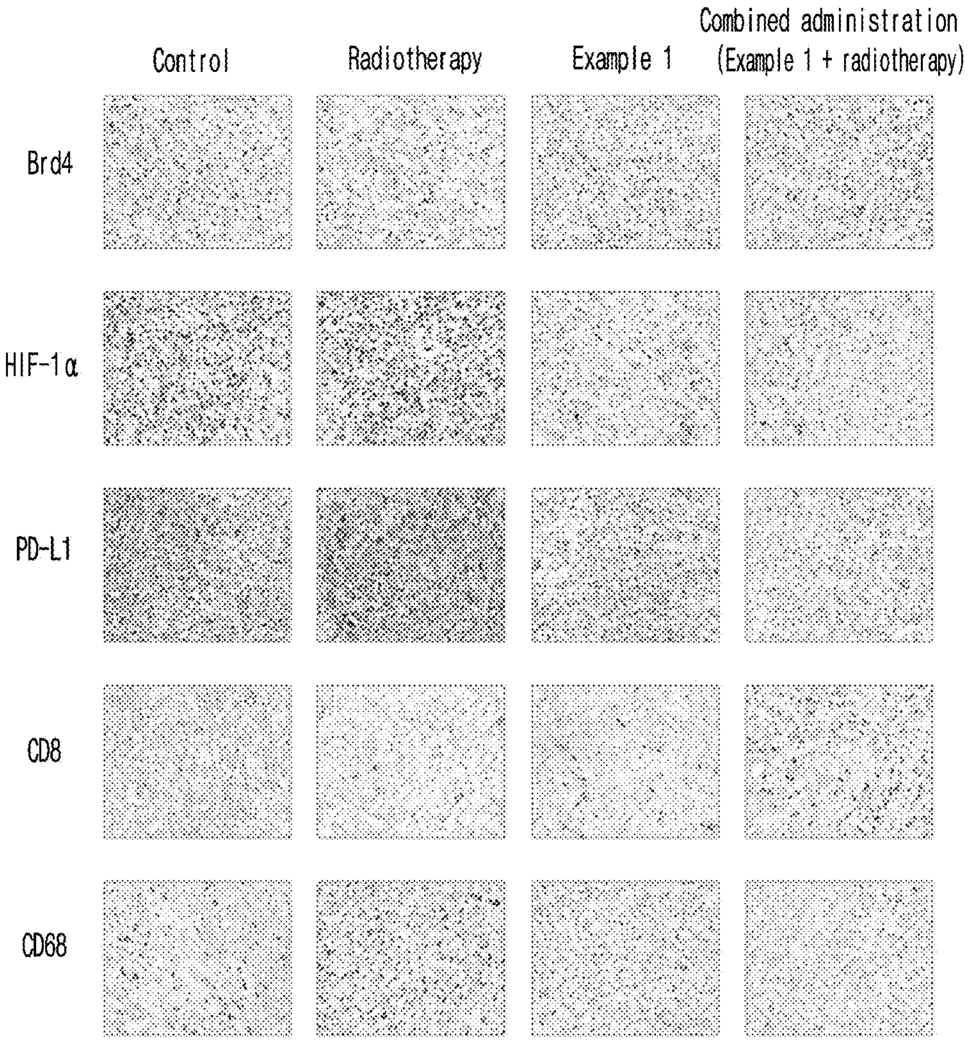
FIG. 16 is a set of photographs showing the results of observing the changes in protein expression and immune cells in tumor cells through immunocytochemical assay.
Figure 17A:
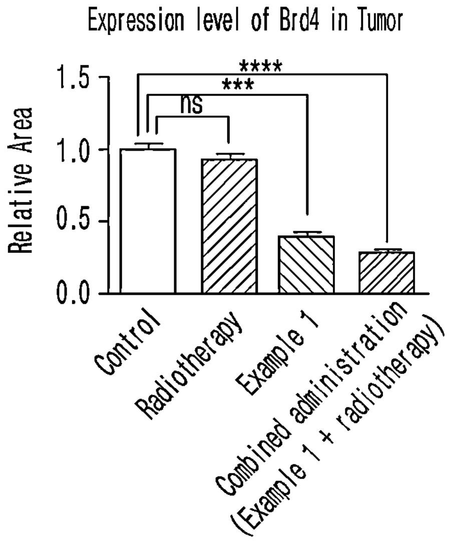
FIGS. 17A-17E are graphs showing the changes in protein expression and immune cells in the tumor cells of FIG. 16 through immunocytochemical assay.
Figure 17B:
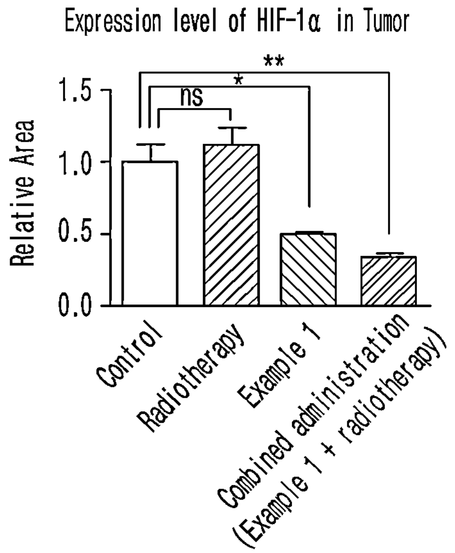
Figure 17C:
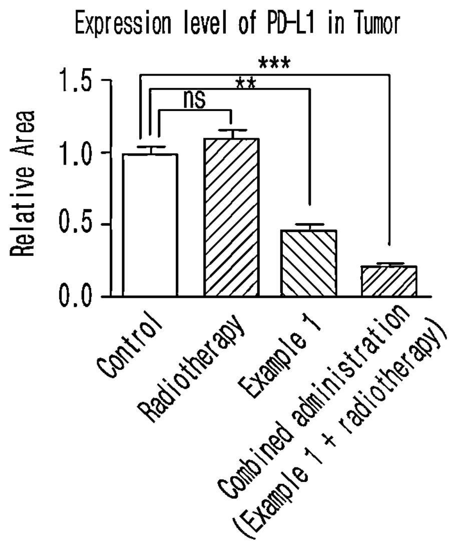
Figure 17D:
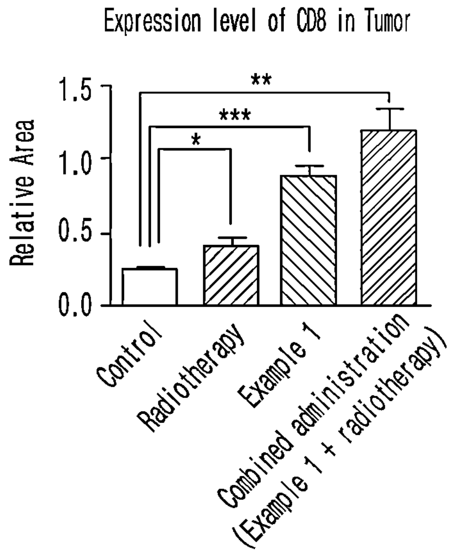
Figure 17E:
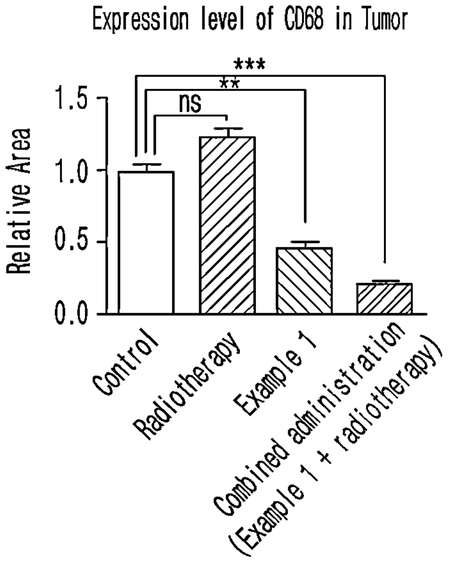

Example 9: Evaluation of Lung Metastasis According to Treatment Method in Triple-Negative Breast Cancer Allograft Mouse Model Mice were prepared in the same manner as in Example 8, and the lungs of the mice were removed on the 31st day after tumor injection, and the results of observing lung metastasis are shown in FIG. 13. As a result, it was confirmed that the administration of the compound of Example 1 alone significantly reduced metastasis compared to the control group. In addition, it was also confirmed that the combined administration of the compound of Example 1 and radiation significantly ($P<0.05$) reduced lung metastases compared to each administration alone.

Example 10: Evaluation of Immune Cell Changes in Tumor Microenvironment According to Treatment Method in Triple-Negative Breast Cancer Allograft Mouse Model The tumor tissues from each mouse were subjected to single cell isolation, followed by flow cytometric analysis (FACS) to confirm the immunomodulatory effect.

Specifically, the spleen and tumor of the mouse were extracted 31 days after tumor cell injection in the same manner as in Example 8. After the tumor tissue was excised, it was mechanically processed by fine chopping using a sterilized razor blade, and then treated with DNase (0.1 mg/ml) and collagenase (1 mg/ml), respectively, and reacted at 36° C. for 30 minutes to obtain a single cell suspension. To analyze infiltrating leukocytes after isolation of single cells from the tumor tissue, 1×10 cells per FACS tube were stained with FITC, PE, PerCP/Cy5.5, and APC fluorescence using CD3 antibody, CD8b antibody, CD4 antibody, CD11b antibody, F4/80 antibody, and CD206 antibody. For each stained sample, the fraction of CD8+ cytotoxic T cells was calculated using BD Bioscience FACSCalibur machines. Analysis of the FACS results was performed using FlowJo software, version 10.

The observed changes in immune cells in the tumor microenvironment according to the treatment method as described above are shown in FIGS. 14 and 15A-15C.

CD+ T cells are known to be cytotoxic T cells that can destroy tumor cells. As a result of the above experiment, it was confirmed that the proportion of CD8+ T cells was increased when the compound of Example 1 was administered alone. In addition, it was confirmed that when the compound of Example 1 and radiation were administered in combination, the proportion of CD8+ T cells was significantly increased compared to each administration alone.

When the compound of Example 1 was administered alone, M1 TAM, which has an antitumor effect, was significantly ($P<0.01$) increased, and M2 TAM, which has an immunosuppressive effect, was significantly ($P<0.01$) decreased. In addition, an increase of M1 TAM and a decrease of M2 TAM were confirmed when the compound of Example 1 and radiation were administered in combination.

Example 11: Evaluation of Protein Expression Changes in Tumor Microenvironment According to Treatment Method in Triple-Negative Breast Cancer Allograft Mouse Model Bromodomain and extraterminal domain (BET) family proteins have recently become important targets for cancer treatment, and in particular, BRD4, one of the BET family members, is commonly found in hematologic tumors and solid tumors. Therefore, in addition to the effect of down-regulating oncogenes, BRD4 inhibitors inhibit tumor growth by directly suppressing the proliferation of tumor cells. In addition, the hypoxia-inducible factor-1α (HIF-1α) protein is a key factor that regulates tumor cell division, angiogenesis, invasion, and metastasis in the tumor microenvironment.

In order to evaluate changes in the expression of proteins such as BRD4 and HIF-1α, the tumor cells isolated in Example 10 were subjected to immunocytochemistry (IHC) analysis to evaluate the changes in protein expression in the tumor microenvironment according to the treatment method. The results are shown in FIGS. 16 and 17A-17E.

Specifically, tumor tissue was extracted, fixed in 4% paraformaldehyde, and embedded in paraffin to create blocks. The paraffin block containing the tissue was sliced transversely to a thickness of 4 μm and attached to a slide. Paraffin was removed from the tissue attached to the slide using xylene and ethanol, and endogenous peroxidase was removed from the tissue by immersing the slide in a solution of 3% $H_2O_2$ in methanol for 10 minutes at room temperature. Then, for antigen retrieval, the slide was placed in 0.01 M sodium citrate buffer (pH 6.0) and boiled. In order to eliminate non-specific binding, FcR on the cell surface was blocked using 5% normal goat serum. Then, the slide was incubated overnight at 4° C. with primary antibodies (HIF-1a (SantaCruz, sc-13515), PD-L1 (Abcam, ab2025921), CD8 (Abcam, ab203035), and CD68 (CellSignaling, 97778)). Secondary antibodies were attached and color development was induced using ImmPRESSGoat Anti-Rat IgG (Mouse Adsorbed) Polymer kit (Vector Laboratories), Abcam (ab150165, ab150081), and REAL En Visiondetection system (Dako). The stained tissue was observed under an Axioskop40 optical microscope (Carl Zeiss) at 40× magnification, and the images were saved using AxioVision4.7 software. The expression level was measured through the area of the stained region in the photograph using Image J software (NIH, Bethesda). Average density values were calculated from at least three slides per sample.

As a result, Brd4 expression was significantly ($P<0.001$) reduced by treatment with the compound of Example 1, and HIF-1α expression, known to be associated with Brd4, was also significantly ($P<0.05$) reduced in the tumor tissue. In addition, it was confirmed that the compound of Example 1 significantly ($P<0.01$) decreased the expression of PD-L1, which is expressed by cancer cells to induce immune evasion.

Consistent with the flow cytometry results of Example 10, it was observed that the population of CD8+ T cells was increased due to radiation and administration of the compound of Example 1, respectively. In addition, it was confirmed that when the compound of Example 1 and radiation were administered in combination, the population of CD8+ T cells was further increased (synergistic effect). Furthermore, the population of CD68+ macrophages in the tumor tissue was significantly ($P<0.01$) reduced by the compound of Example 1.

Figure 18A:
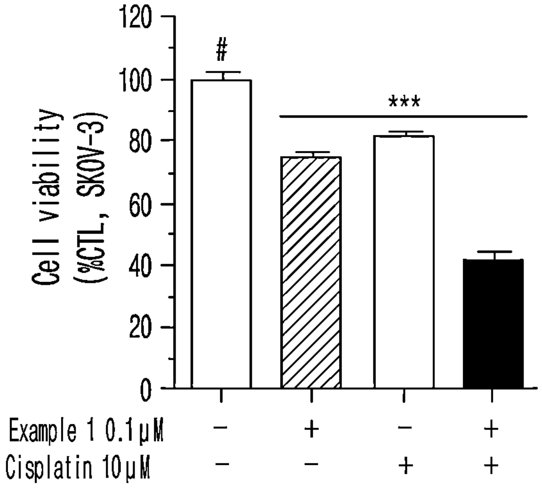
FIGS. 18A-18B are graphs showing the cell viability of tumor cells (SKOV-3 and OVCAR-3) upon administration of the compound of Example 1 and cisplatin alone and in combination.
Figure 18B:
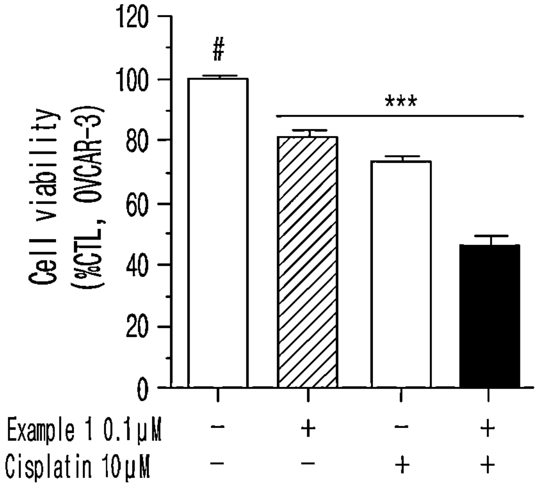

Example 12: Evaluation of Efficacy in Combination with Other Anticancer Agents <11-1> Evaluation of Efficacy in Combination with Cisplatin Human ovarian cancer cell lines (SKOV-3 and OVCAR-3) were treated with control (no treatment), 0.1 μM of the compound of Example 1, 1 μM of cisplatin, and 0.1 μM of the compound of Example 1/1 μM of cisplatin, and the cell viability of SKOV-3 and OVCAR-3 was confirmed. The results are shown in FIGS. 18A-18B.

It was confirmed that the cell viability was suppressed when 0.1 μM of the compound of Example 1 or 1 μM of cisplatin was administered to SKOV-3 and OVCAR-3 cell lines. In addition, it was also confirmed that when 0.1 μM of the compound of Example 1 and 1 μM of cisplatin were administered in combination, the cell viability was further inhibited (synergistic effect).

<11-2> Evaluation of Efficacy in Combination with Sorafenib

Figure 19A:
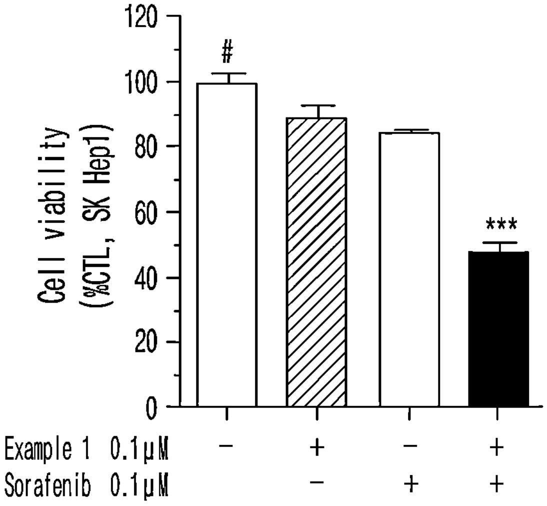
FIGS. 19A-19B are graphs showing the cell viability of tumor cells (SK Hep1 and Huh-7) upon administration of the compound of Example 1 and sorafenib alone and in combination.
Figure 19B:
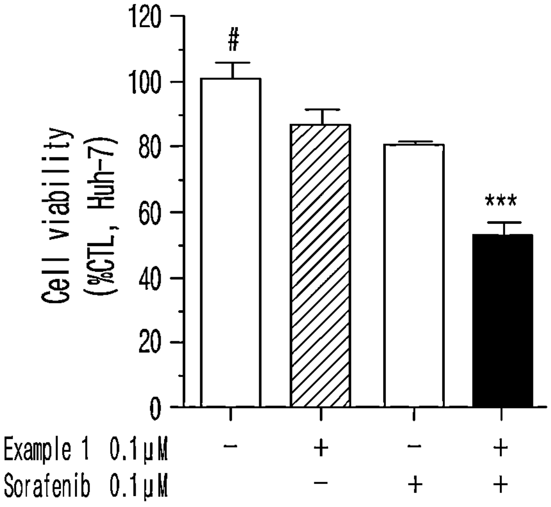

Human liver cancer cell lines (SK Hep1 and Huh-7) were treated with control (no treatment), 0.1 μM of the compound of Example 1, 1 μM of sorafenib, and 0.1 μM of the compound of Example 1/1 μM of sorafenib, and the cell viability of SK Hep1 and Huh-7 was confirmed. The results are shown in FIGS. 19A-19B.

It was confirmed that the cell viability was suppressed when 0.1 μM of the compound of Example 1 or 1 μM of sorafenib was administered to SK Hep1 and Huh-7 cell lines. In addition, it was also confirmed that when 0.1 μM of the compound of Example 1 and 1 μM of sorafenib were administered in combination, the cell viability was further inhibited (synergistic effect).

From the above results, it was confirmed that the compound of Example 1 according to the present invention inhibits the formation of mammospheres in a breast cancer cell line and, when compared to anticancer drugs sorafenib and etoposide, which are topoisomerase inhibitors widely used in lung cancer, ovarian cancer, colon cancer, melanoma and the like, exhibits remarkable effects greater than or equal to those of the anticancer drugs sorafenib and etoposide. In addition, the compound of Example 1 according to the present invention exhibits synergistic anticancer effects when combined with radiotherapy or other anticancer drugs in a breast cancer cell line and a liver cancer cell line, and thus can be developed as an anticancer drug or a food exhibiting excellent effects in the treatment of cancer.

What is claimed is:

1. A method for preventing or treating cancer comprising a step of administering an effective amount of a compound represented by formula 1 below, a stereoisomer thereof, a solvate thereof, a hydrate thereof, or a pharmaceutically acceptable salt thereof to a subject in need thereof:

[Formula 1]

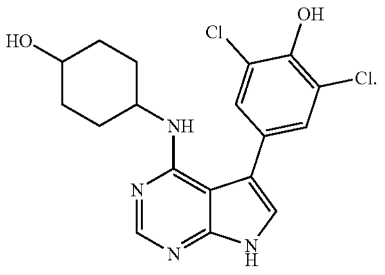

2. The method for preventing or treating cancer according to claim 1, wherein the compound represented by formula 1 above is (trans)-2,6-dichloro-4-(4-(4-hydroxycyclohexylamino)-7H-pyrrolo[2,3-D]pyrimidin-5-yl)phenol.

3. The method for preventing or treating cancer according to claim 1, wherein the cancer is anyone selected from the group consisting of lung cancer, non-small cell lung cancer (NSCL), bronchial alveolar cell lung cancer, ovarian cancer, colorectal cancer, melanoma, stomach cancer, gastrointestinal cancer, liver cancer, bone cancer, pancreatic cancer, skin cancer, head and neck cancer, skin or eye melanoma, uterine cancer, rectal cancer, colon cancer, breast cancer, uterine sarcoma, fallopian tube carcinoma, endometrial carcinoma, cervical carcinoma, vaginal carcinoma, vulvar carcinoma, esophageal cancer, laryngeal cancer, small intestine cancer, thyroid cancer, parathyroid cancer, soft tissue sarcoma, urethral cancer, penile cancer, prostate cancer, multiple myeloma, and chronic or acute leukemia.

4. The method for preventing or treating cancer according to claim 3, wherein the cancer is breast cancer or liver cancer.

5. The method for preventing or treating cancer according to claim 1, wherein the compound represented by formula 1, a stereoisomer thereof, a solvate thereof, a hydrate thereof, or a pharmaceutically acceptable salt is used for combined treatment with radiation or anticancer agents.

6. The method for preventing or treating cancer according to claim 5, wherein the anticancer agent is at least one selected from the group consisting of cisplatin, sorafenib, opdivo, tecentriq, keytruda, imfinzi, OKN-007 (Oklahoma nitrone-007), gefitinib, doxorubicin, vinblastine, taxol, etoposide, 5-FU (5-Fluorouracil), and ifosfamide.

7. The method for preventing or treating cancer according to claim 1, wherein the compound represented by formula 1, a stereoisomer thereof, a solvate thereof, a hydrate thereof, or a pharmaceutically acceptable salt enhances immunity.

8. A pharmaceutical kit for preventing or treating cancer comprising a first component containing a pharmaceutically effective amount of an anticancer agent; and a second component containing a compound represented by formula 1 below, a stereoisomer thereof, a solvate thereof, a hydrate thereof, or a pharmaceutically acceptable salt thereof as an active ingredient:

[Formula 1]

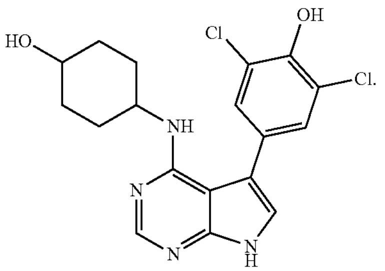

9. The pharmaceutical kit for preventing or treating cancer according to claim 8, wherein the compound represented by formula 1 above is (trans)-2,6-dichloro-4-(4-(4-hydroxycyclohexylamino)-7H-pyrrolo[2,3-D]pyrimidin-5-yl)phenol.

10. The pharmaceutical kit for preventing or treating cancer according to claim 8, wherein the cancer is anyone selected from the group consisting of lung cancer, non-small cell lung cancer (NSCL), bronchial alveolar cell lung cancer, ovarian cancer, colorectal cancer, melanoma, stomach cancer, gastrointestinal cancer, liver cancer, bone cancer, pancreatic cancer, skin cancer, head and neck cancer, skin or eye melanoma, uterine cancer, rectal cancer, colon cancer, breast cancer, uterine sarcoma, fallopian tube carcinoma, endometrial carcinoma, cervical carcinoma, vaginal carcinoma, vulvar carcinoma, esophageal cancer, laryngeal cancer, small intestine cancer, thyroid cancer, parathyroid cancer, soft tissue sarcoma, urethral cancer, penile cancer, prostate cancer, multiple myeloma, and chronic or acute leukemia.

11. The pharmaceutical kit for preventing or treating cancer according to claim 8, wherein the anticancer agent is at least one selected from the group consisting of cisplatin, sorafenib, opdivo, tecentriq, keytruda, imfinzi, OKN-007 (Oklahoma nitrone-007), gefitinib, doxorubicin, vinblastine, taxol, etoposide, 5-FU (5-fluorouracil), and ifosfamide.

12. A method for preventing or treating cancer, comprising a step of co-administering i) an effective amount of a compound represented by formula 1 of claim 1, a stereoisomer thereof, a solvate thereof, a hydrate thereof, or a pharmaceutically acceptable salt thereof to a subject in need thereof and ii) radiation or anticancer agent to a subject in need thereof.

* * * * *